US008978055B1

(12) United States Patent
Sudo et al.

(10) Patent No.: US 8,978,055 B1
(45) Date of Patent: Mar. 10, 2015

(54) ELECTRONIC APPARATUS AND METHOD

(71) Applicant: Kabushiki Kaisha Toshiba, Tokyo (JP)

(72) Inventors: Takashi Sudo, Fuchu (JP); Yasuhiro Kanishima, Tokyo (JP); Shingo Suzuki, Sagamihara (JP); Toyokazu Itakura, Kawasaki (JP); Kentaro Takeda, Tokyo (JP); Takaya Matsuno, Kunitachi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/185,694

(22) Filed: Feb. 20, 2014

(51) Int. Cl.
H04N 7/16 (2011.01)
H04H 60/33 (2008.01)
H04H 60/56 (2008.01)
G06F 3/00 (2006.01)
G06F 13/00 (2006.01)
H04N 5/445 (2011.01)
H04N 21/442 (2011.01)

(52) U.S. Cl.
CPC ... *H04N 21/44204* (2013.01); *H04N 21/44218* (2013.01)
USPC .................. 725/10; 725/12; 725/39

(58) Field of Classification Search
None
See application file for complete search history.

(56) References Cited

U.S. PATENT DOCUMENTS

| 5,918,014 | A | * | 6/1999 | Robinson | 709/219 |
| 7,930,722 | B2 | * | 4/2011 | Pepper et al. | 725/78 |
| 8,094,236 | B2 | | 1/2012 | Tanaka et al. | |
| 2003/0229446 | A1 | * | 12/2003 | Boscamp et al. | 701/213 |
| 2005/0289611 | A1 | * | 12/2005 | Taki | 725/75 |
| 2006/0090180 | A1 | * | 4/2006 | Uz | 725/39 |
| 2007/0038727 | A1 | * | 2/2007 | Bailey et al. | 709/219 |
| 2007/0236615 | A1 | | 10/2007 | Tanaka et al. | |
| 2012/0105725 | A1 | | 5/2012 | Tanaka et al. | |

FOREIGN PATENT DOCUMENTS

| JP | 2003-044960 | 2/2003 |
| JP | 2007-058404 | 3/2007 |
| JP | 2012-055471 | 3/2012 |
| JP | 2012-105353 | 5/2012 |
| JP | 2012-226780 | 11/2012 |
| JP | 2013-054595 | 3/2013 |

* cited by examiner

*Primary Examiner* — Oschta Montoya
(74) *Attorney, Agent, or Firm* — Blakely, Sokoloff, Taylor & Zafman LLP

(57) ABSTRACT

According to one embodiment, an electronic apparatus includes a receiver, a generator and a transmitter. The receiver receives operation data indicative of an operating period from each of one or more electronic apparatuses used by a first user, and receives viewing data from a first electronic apparatus of the one or more electronic apparatuses, the viewing data indicative of a program viewed by the first user. The generator generates living pattern data indicative of a living pattern of the first user using the operation data and the viewing data. The transmitter transmits the living pattern data to an electronic apparatus used by a second user.

10 Claims, 25 Drawing Sheets

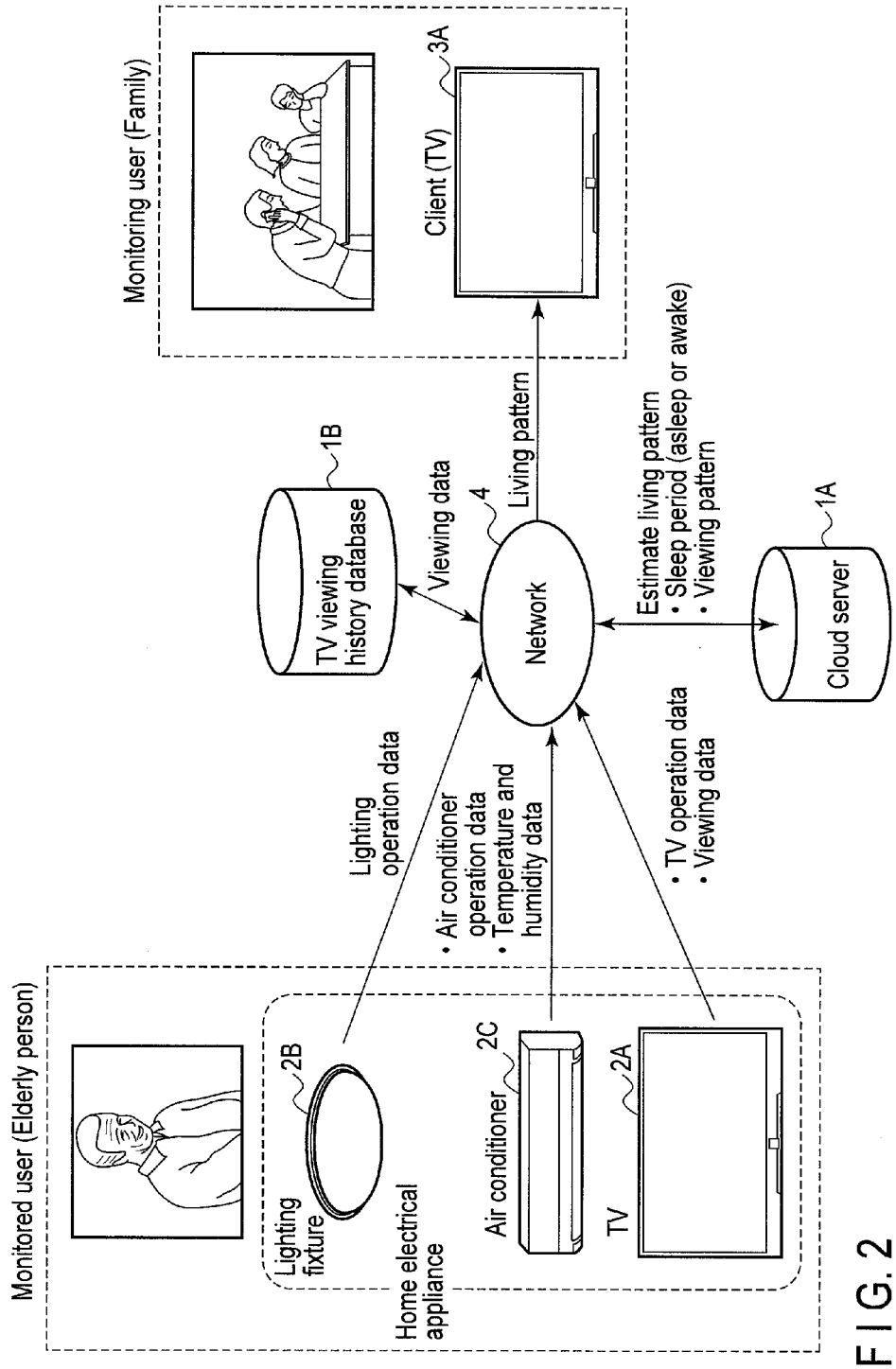
F I G. 2

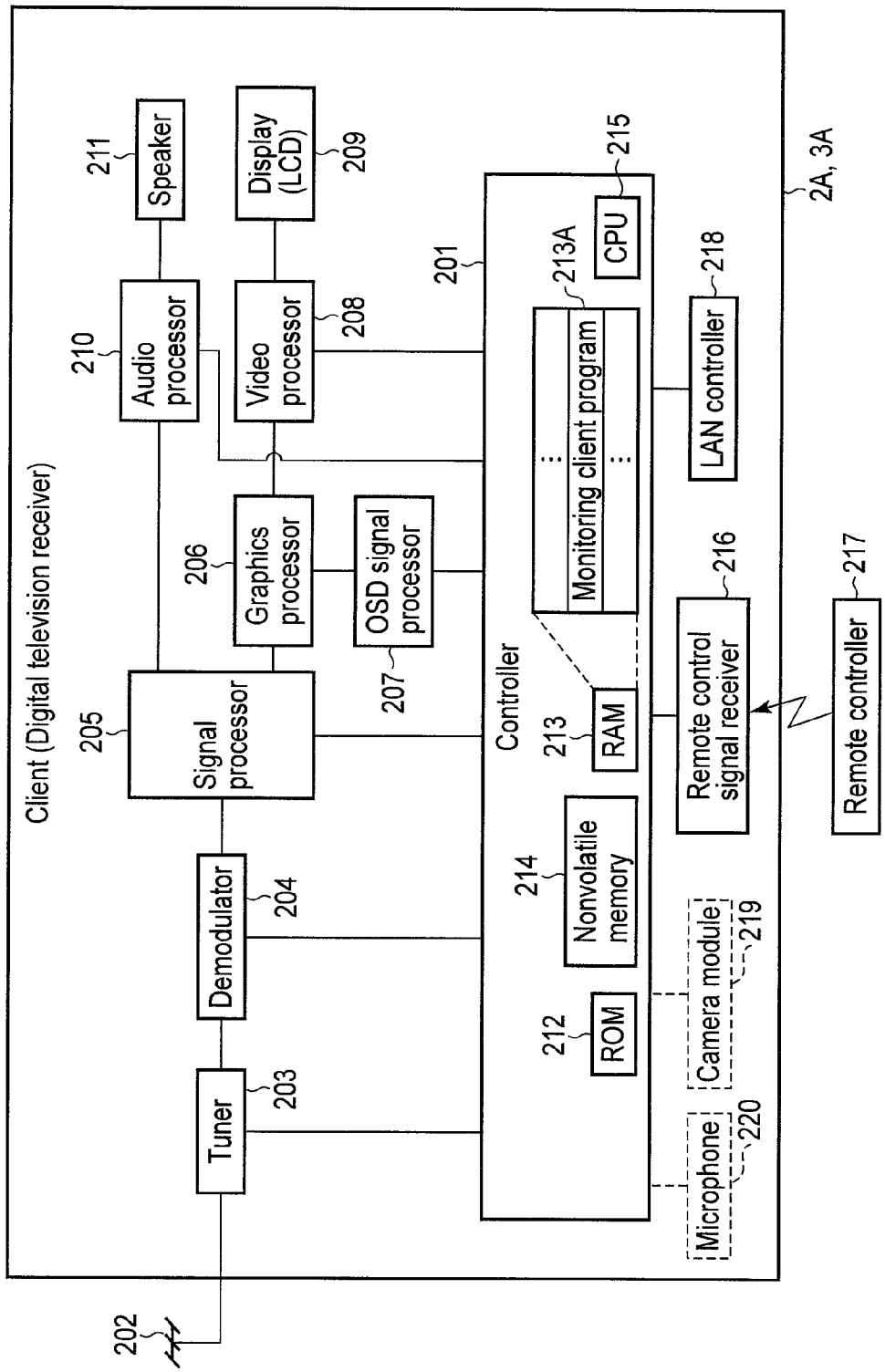
F I G. 5

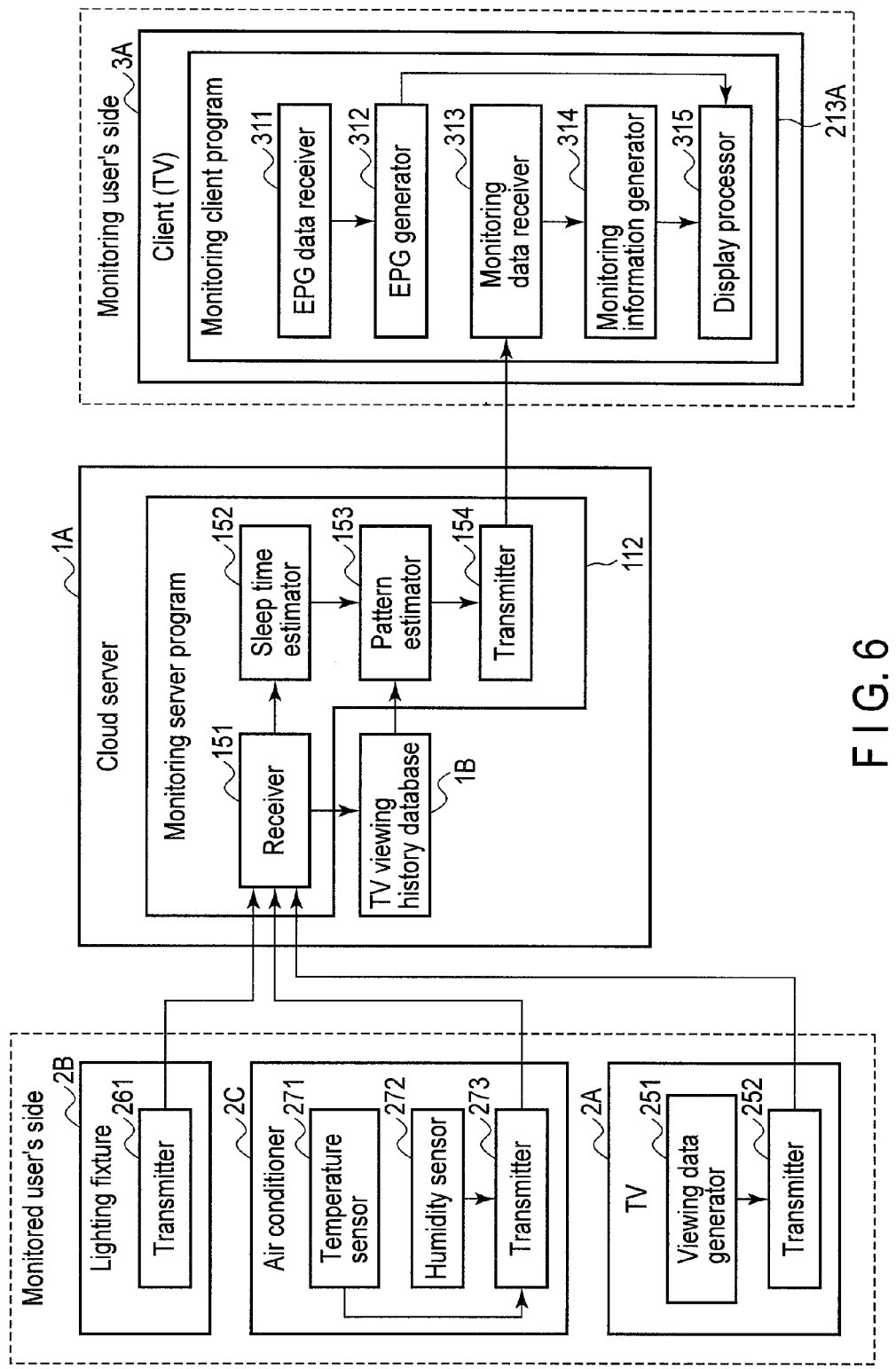
F I G. 6

| User ID | Date | Lighting operating period | Air conditioner operating period | Temperature | Humidity | TV operating period | ... |
|---|---|---|---|---|---|---|---|
| ... | ... | ... | ... | ... | ... | ... | ... |
| ... | ... | ... | ... | ... | ... | ... | ... |
| ⋮ | ⋮ | ⋮ | ⋮ | ⋮ | ⋮ | ⋮ | ⋮ |

FIG. 7

| User ID | Date | Time | Channel | Program title | Viewing status | Category | Degree of smile | Biorhythm | ... |
|---|---|---|---|---|---|---|---|---|---|
| ... | ... | ... | ... | ... | ... | ... | ... | ... | ... |
| ... | ... | ... | ... | ... | ... | ... | ... | ... | ... |
| ⋮ | ⋮ | ⋮ | ⋮ | ⋮ | ⋮ | ⋮ | ⋮ | ⋮ | ⋮ |

FIG. 8

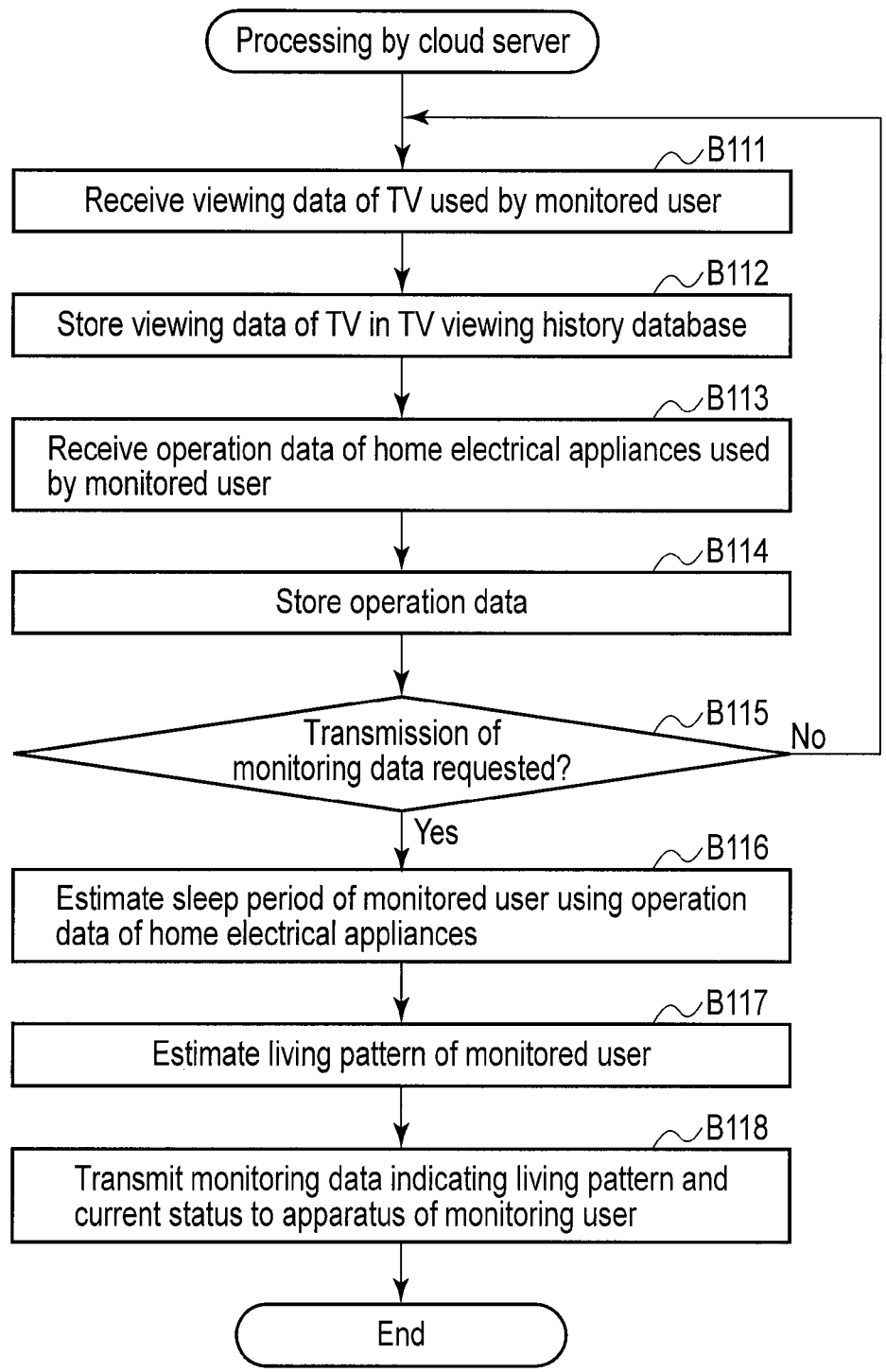
F I G. 1 0

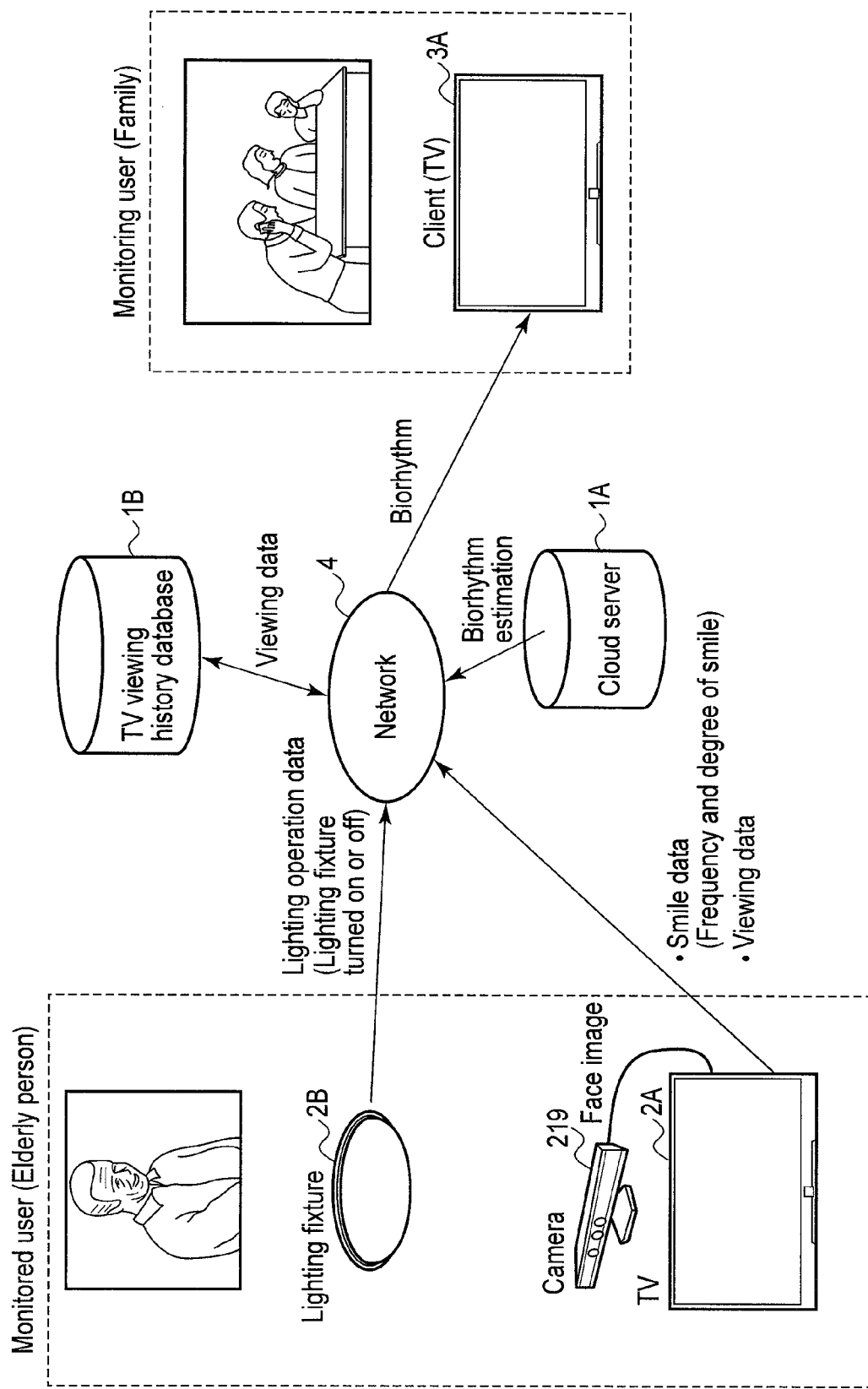
F I G. 12

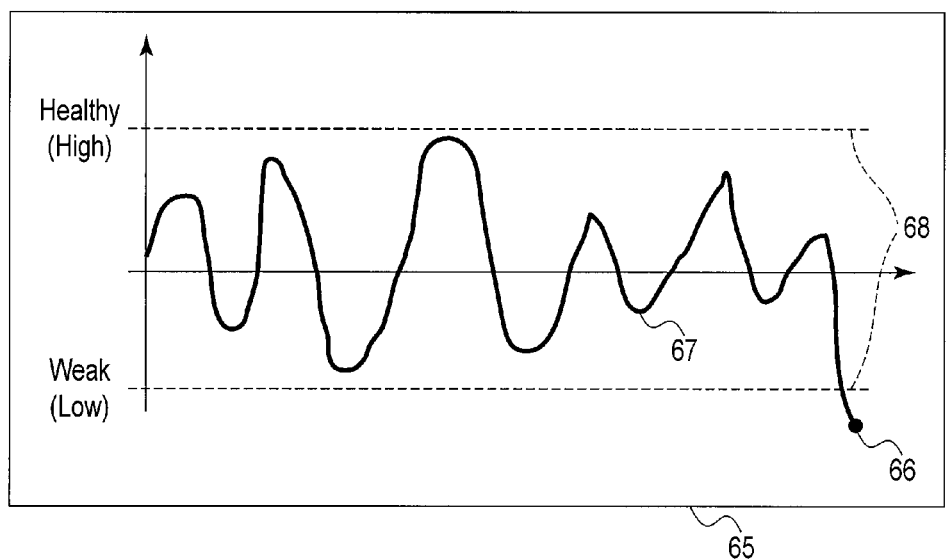
F I G. 13

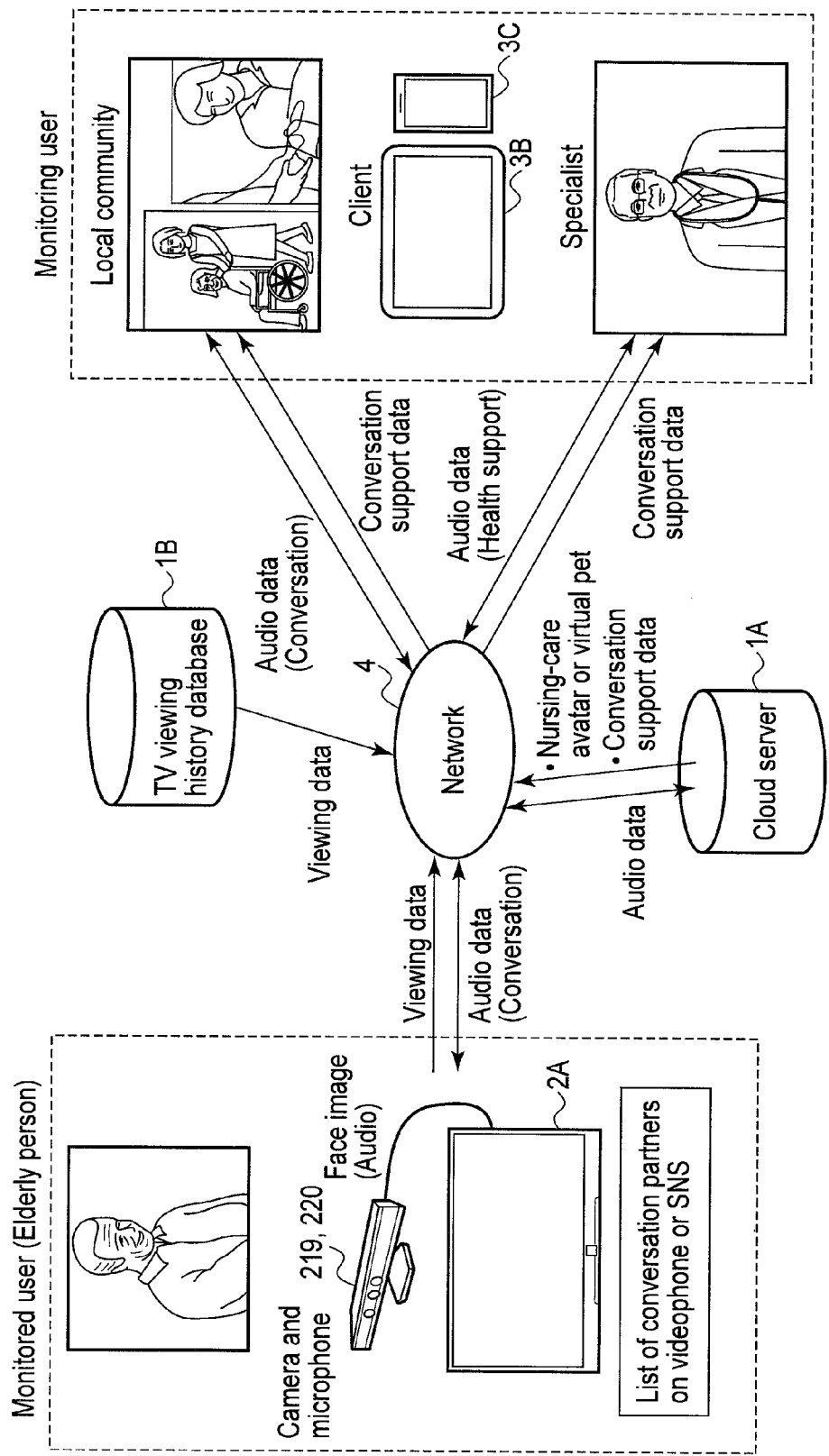
F I G. 18

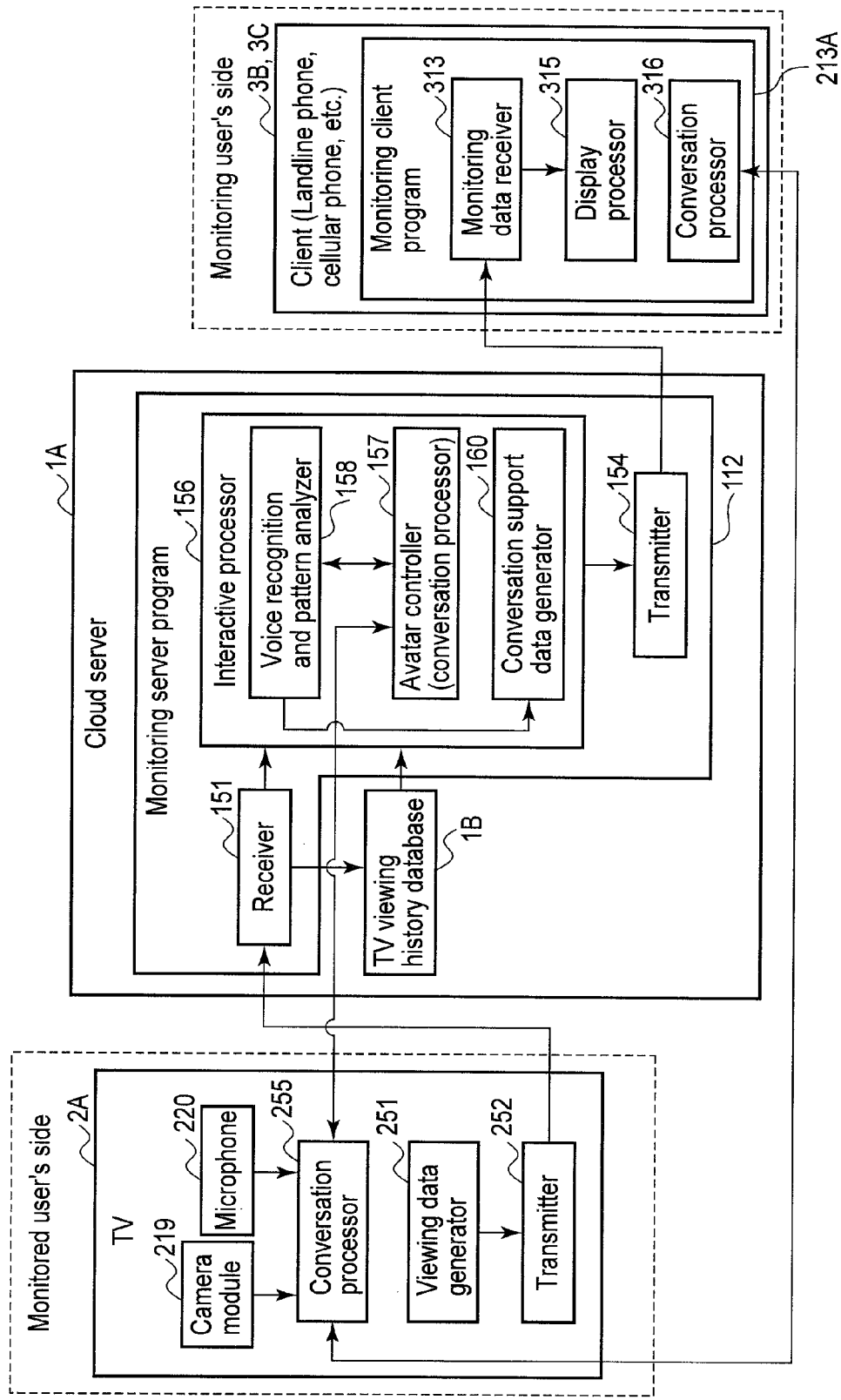
F I G. 19

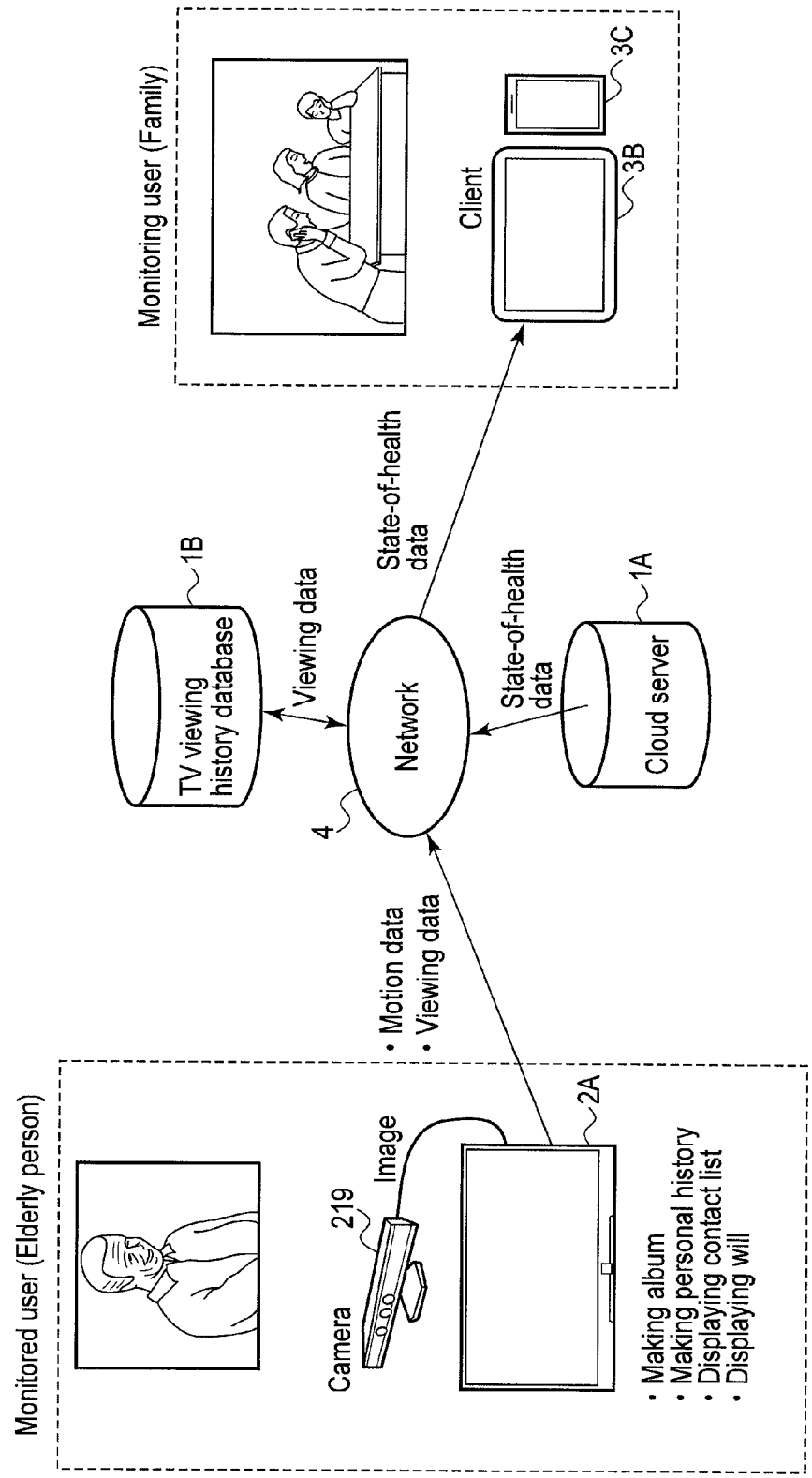
F I G. 2 3

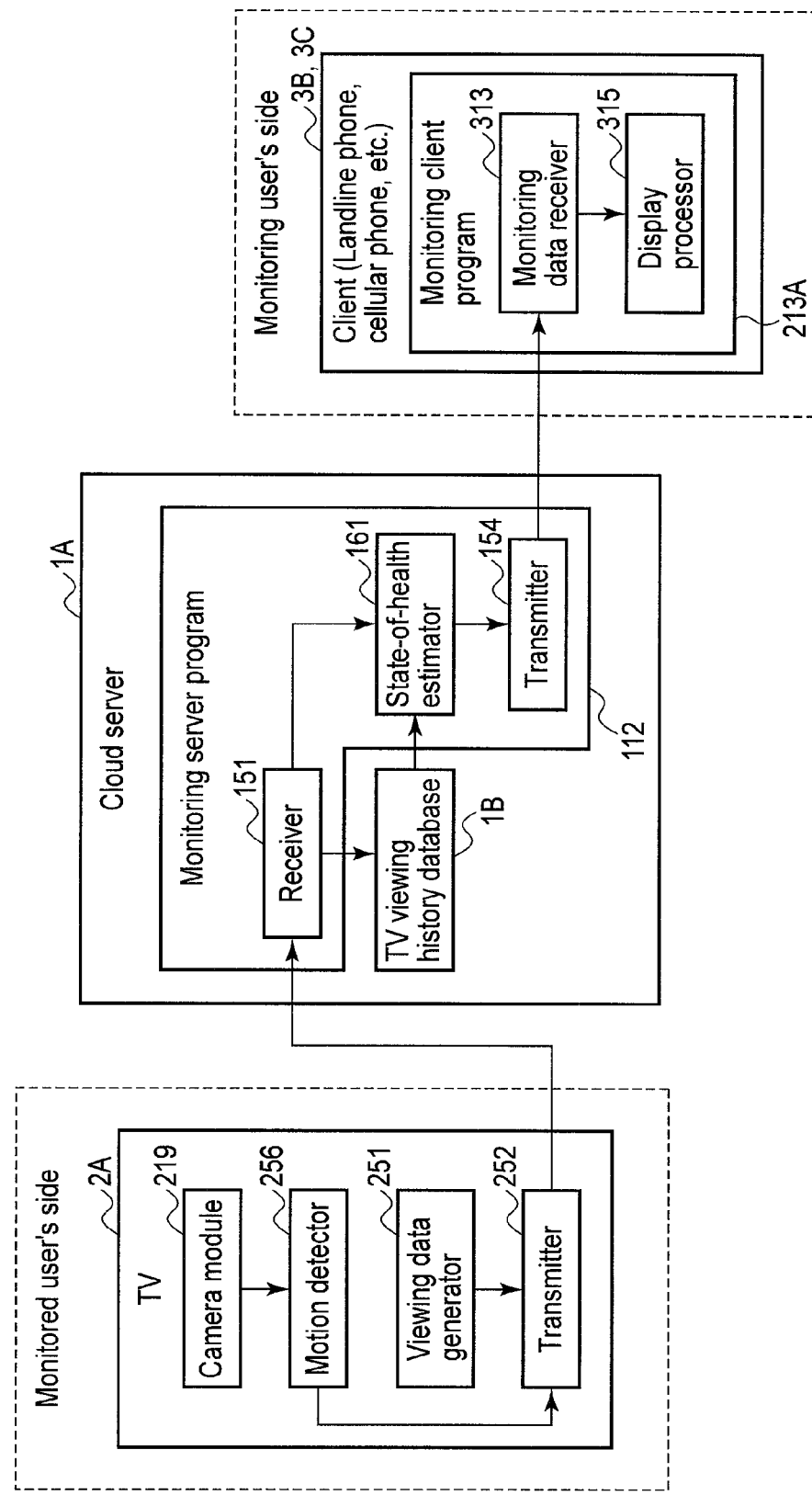
F I G. 24

ELECTRONIC APPARATUS AND METHOD

CROSS-REFERENCE TO RELATED APPLICATIONS

This application is based upon and claims the benefit of priority from Japanese Patent Application No. 2013-203421, filed Sep. 30, 2013, the entire contents of which are incorporated herein by reference.

FIELD

Embodiments described herein relate generally to an electronic apparatus for supporting monitoring at a remote place and a method applied to the apparatus.

BACKGROUND

If an elderly person and their family live apart from each other, the family will be anxious to ensure that the elderly person is staying in good health by making sure that the elderly person's daily routine is normal. The family can do this by monitoring the elderly person's daily activities by means of a system in which, for example, the activities are captured by a video camera and the captured video is transmitted to an electronic apparatus such as a personal computer used by the family.

However, being able to be seen by others disturbs the peace of mind of the elderly person (monitored user). In addition, regularly monitoring the elderly person causes the family (monitoring user) to feel guilty. In other words, invasion of privacy problem is an issue with such a system.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 2 is a schematic view illustrating an example of indicating a living pattern of a monitored user to a monitoring user by the electronic apparatus according to the embodiment.

FIG. 5 is a block diagram illustrating an example of the system configuration of the electronic apparatus used by the monitoring user of FIG. 2.

FIG. 6 is a block diagram illustrating a first example of a functional configuration of the electronic apparatus according to the embodiment.

FIG. 7 illustrates a configuration example of operation data of a home electrical appliance used by the electronic apparatus according to the embodiment.

FIG. 8 illustrates a configuration example of viewing history data used by the electronic apparatus according to the embodiment.

FIG. 10 is a flowchart illustrating a first example of the procedure of a process executed by the electronic apparatus according to the embodiment.

FIG. 12 is a schematic view illustrating an example of indicating a biorhythm of the monitored user to the monitoring user by the electronic apparatus according to the embodiment.

FIG. 13 illustrates an example of the screen displayed on the electronic apparatus (TV) used by the monitoring user using the biorhythm indicated by the electronic apparatus according to the embodiment.

FIG. 18 is a schematic view illustrating an example of providing the monitoring user with conversation support data of the monitored user by the electronic apparatus according to the embodiment.

FIG. 19 is a block diagram illustrating a third example of the functional configuration of the electronic apparatus according to the embodiment.

FIG. 23 is a schematic view illustrating an example of providing the monitoring user with state-of-health data of the monitored user by the electronic apparatus according to the embodiment.

FIG. 24 is a block diagram illustrating a fourth example of the functional configuration of the electronic apparatus according to the embodiment.

DETAILED DESCRIPTION

Various embodiments will be described hereinafter with reference to the accompanying drawings.

In general, according to one embodiment, an electronic apparatus includes a receiver, a generator and a transmitter. The receiver is configured to receive operation data indicative of an operating period from each of one or more electronic apparatuses used by a first user, and to receive viewing data from a first electronic apparatus of the one or more electronic apparatuses, the viewing data indicative of a program viewed by the first user. The generator is configured to generate living pattern data indicative of a living pattern of the first user using the operation data and the viewing data. The transmitter is configured to transmit the living pattern data to an electronic apparatus used by a second user.

Figure 1:
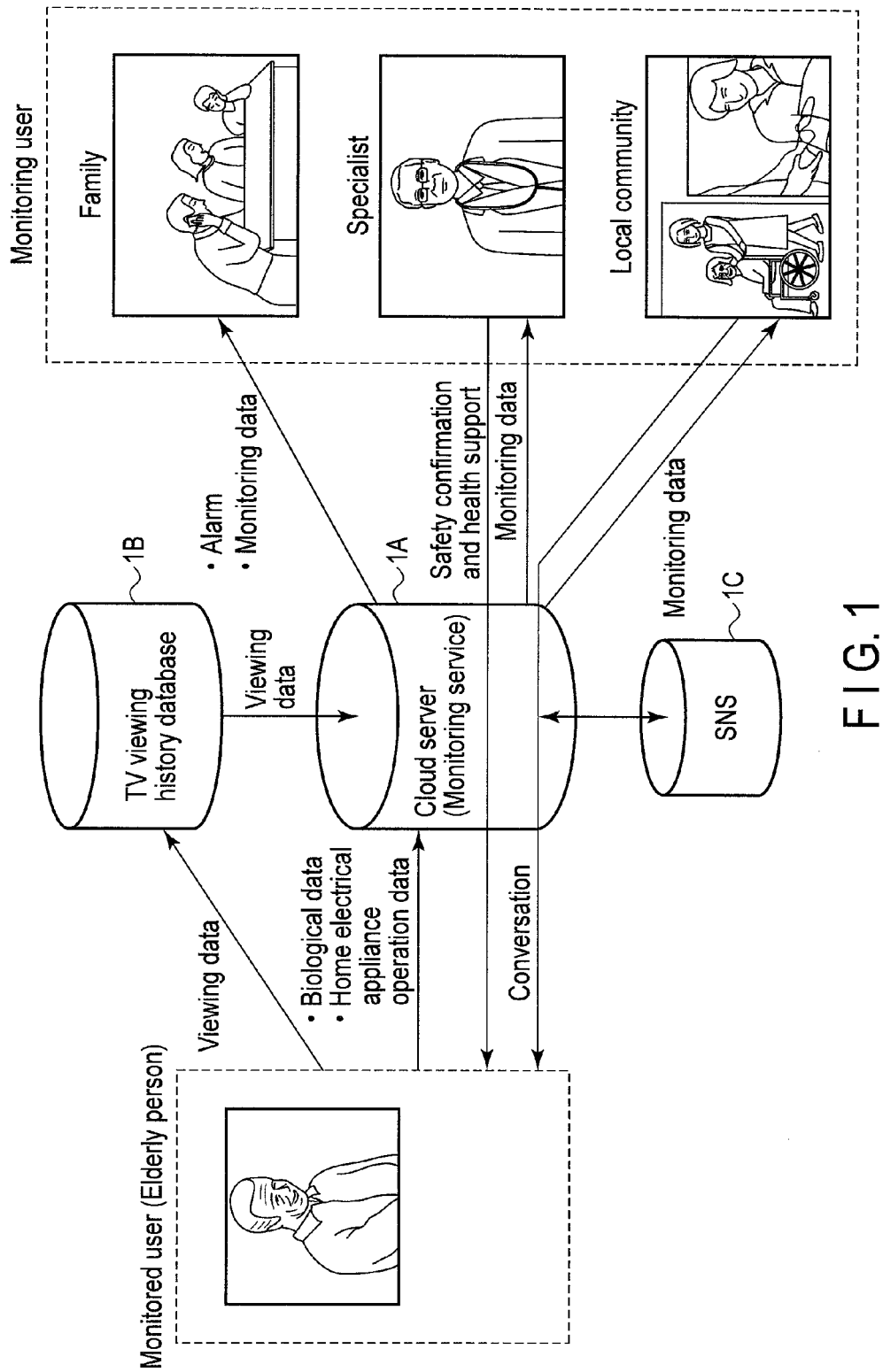
FIG. 1 is an exemplary schematic view illustrating a monitoring system including an electronic apparatus (cloud server) according to an embodiment.

First, an overview of a monitoring system including an electronic apparatus according to an embodiment will be described with reference to FIG. 1. The electronic apparatus is a cloud server 1A which provides a monitoring user in a remote location (for example, the family of a monitored person, a specialist such as a doctor and a careworker, a local community organization, etc.) with information (monitoring data) for monitoring the monitored person using data concerning the monitored user (for example, elderly person). The cloud server 1A is realized as, for example, a server computer.

The cloud server 1A receives operation data and biological data from various electronic apparatuses used by the monitored user, and receives viewing data of a TV program viewed by the monitored user through a TV viewing history database 1B. It should be noted that the TV viewing history database 1B may be provided in the cloud server 1A. By analyzing the received data, the cloud server 1A, for example, provides a family with information showing the daily routine of an elderly person and an alarm, provides a specialist with information for safety confirmation and health support of the elderly person, and provides a local community organization with information for supporting conversation with the elderly person. It should be noted that the cloud server 1A can provide such information in conjunction with a social networking service (SNS) 1C having information such as friends, hobbies and tastes of the monitored user.

In the monitoring system according to this embodiment, data is collected using a home electrical appliance such as a TV, and information concerning the monitored user is provided based on the data. Thus, casual monitoring can be realized and stress placed on the monitored and monitoring users can be reduced.

FIG. 2 illustrates an example of indicating a living pattern of the monitored user (elderly person) to the monitoring user (family) by the cloud server 1A. Electronic apparatuses (home electrical appliances) 2A, 2B and 2C used by the monitored user transmit operation data, etc., to the cloud server 1A through a network 4.

More specifically, a lighting fixture 2B transmits lighting operation data indicating an operating period based on the on/off state of the lighting fixture 2B to the cloud server 1A. An air conditioner 2C transmits air conditioner operation data indicating the operating period based on the on/off state of the air conditioner 2C, and temperature and humidity data indicating indoor temperature and humidity detected by the air conditioner 2C to the cloud server 1A.

A television receiver (TV) 2A transmits TV operation data indicating the operating period based on the on/off state of the TV to the cloud server 1A. The TV 2A also stores viewing data indicating a program viewed by the monitored user in the TV viewing history database 1B through the network 4. The TV viewing history database 1B accumulates, for example, electronic program guide (EPG) data and the viewing data of the monitored user during a given period. The cloud server 1A receives viewing data indicating a program viewed by the monitored user from the TV viewing history database 1B by accessing the TV viewing history database 1B through the network 4.

The cloud server 1A estimates a living pattern of the monitored user using received data of various home electrical appliances. This living pattern includes, for example, a sleep period based on determination as to whether the monitored user is asleep or awake, a viewing pattern of a TV program by the monitored user, etc. The cloud server 1A transmits data indicating the estimated living pattern of the monitored user to a client 3A used by the monitoring user through the network 4.

The client 3A may be realized as, for example, a television receiver. It should be noted that the client 3A may be realized as a portable information device such as a cellular phone and a smartphone, a personal computer, or a system embedded in various electronic apparatuses. The client 3A receives data indicating the living pattern of the monitored user, and displays information indicating the living pattern of the monitored user on a screen using the data.

Figure 3:
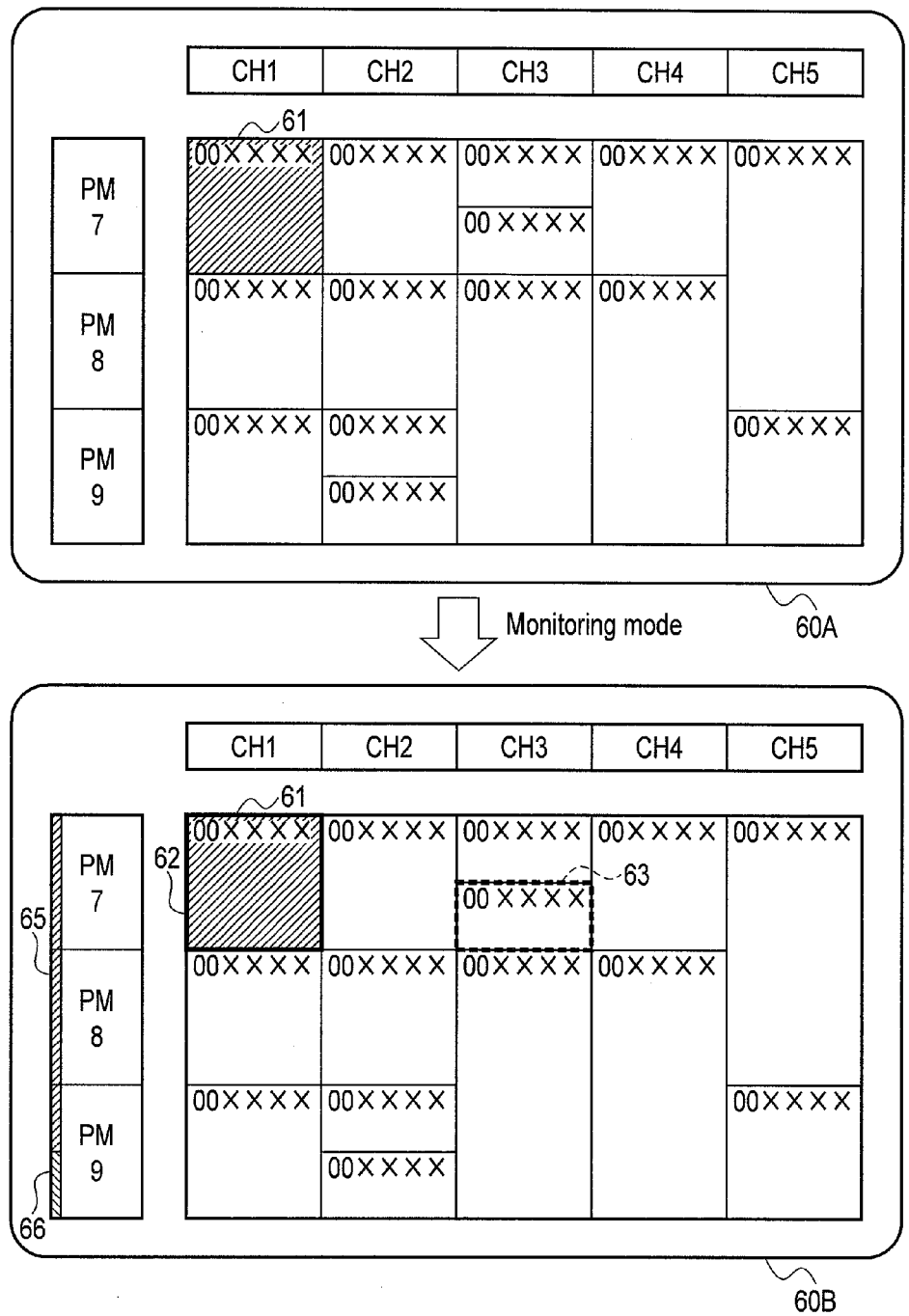
FIG. 3 illustrates an example of a screen displayed on an electronic apparatus (TV) used by the monitoring user using the living pattern indicated by the electronic apparatus according to the embodiment.

FIG. 3 illustrates a case where the client 3A displays information indicating the living pattern of the monitored user (remote user) on an EPG. Suppose the client 3A displays on the screen an EPG 60A including a program 61 currently being viewed by the monitoring user in a display form which can be distinguished from other programs. The area of the program 61 is displayed by, for example, a color, a pattern, a closing line, etc., which are different from the areas of the other programs. The client 3A detects that a shift to a monitoring mode in which information of the monitored user is displayed has been instructed, when the EPG 60A is displayed. The client 3A detects, for example, that the shift to the monitoring mode has been instructed by a user operation using a remote controller.

The client 3A displays an EPG 60B using data indicating the living pattern of the monitored user in response to the detected instruction of the shift to the monitoring mode (that is, the EPG 60A is changed to the EPG 60B). In addition to the program 61 currently being viewed by the monitoring user, a program 62 frequently viewed by the monitored user during a current period and a program 63 currently being viewed by the monitored user are included in the EPG 60B in the display form which can be distinguished from the other programs. In FIG. 3, the program 62 frequently viewed by the monitored user is the same program as the program 61 currently being viewed by the monitoring user. Each of the areas of the programs 61, 62 and 63 are displayed to be distinguished by the monitoring user using a color, a pattern, a closing line, a mark, etc.

It should be noted that the sleep period of the monitored user can also be shown in the EPG 60B of the monitoring mode using the data indicating the living pattern of the monitored user. For example, in the EPG 60B, a period 65 during which the monitored user is awake and a period 66 during which the monitored user is asleep are distinguishably displayed. Further, information indicating whether the monitored user is currently awake or not (mark, etc.) may be displayed in the EPG 60B.

Thus, the monitoring user can be aware of daily activities without directly monitoring the monitored user using video, etc. The monitoring user can check whether something happens to the monitored user or not by, for example, confirming whether the monitored user behaves based on the living pattern in the past or not, with reference to the EPG 60B. In addition, since the EPG 60B is displayed in response to the instruction of the shift to the monitoring mode by the monitoring user, the monitoring user can confirm information only when worried about the condition of the monitored user.

Figure 4:
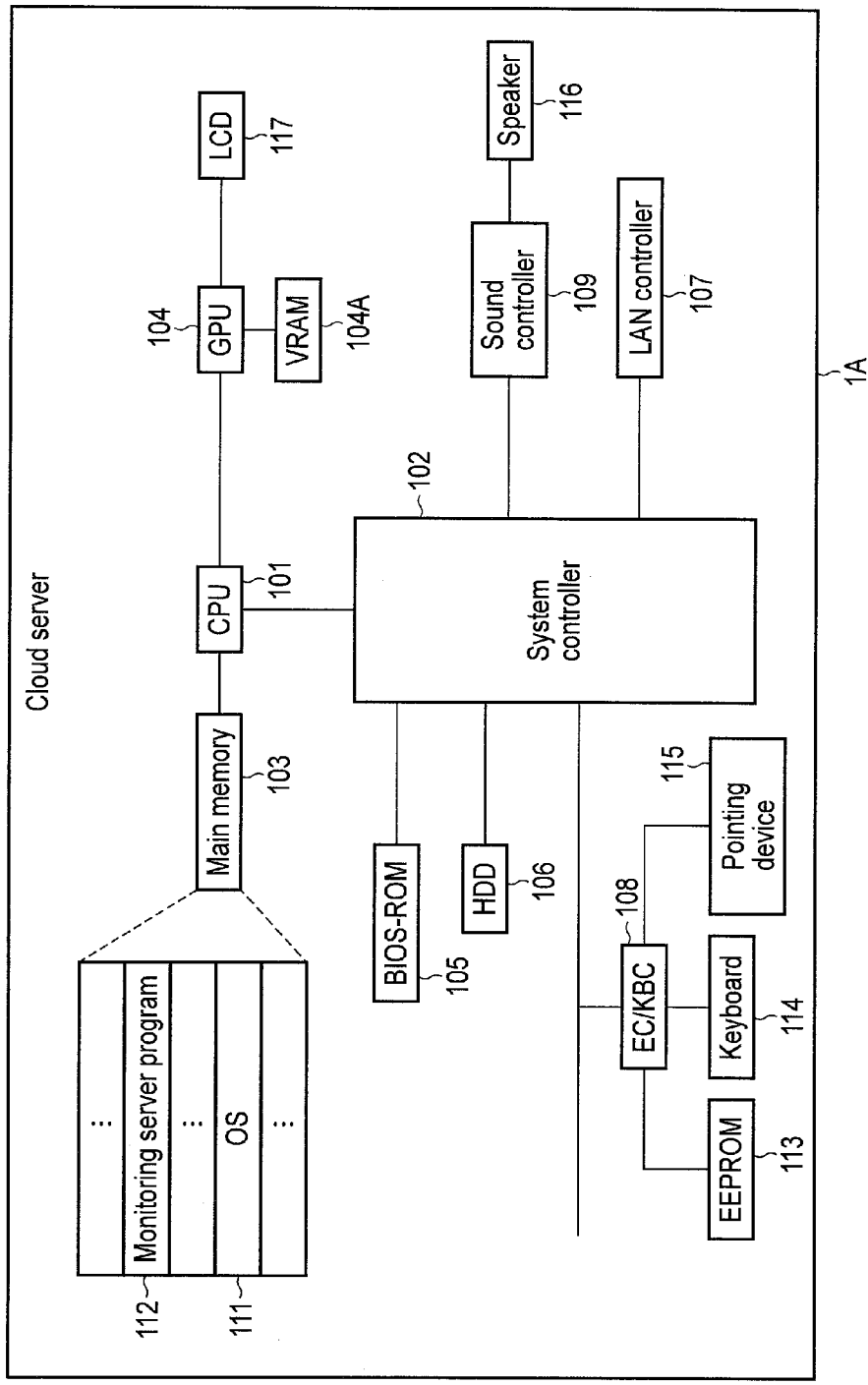
FIG. 4 is a block diagram illustrating an example of a system configuration of the electronic apparatus according to the embodiment.

Next, FIG. 4 illustrates an example of the system configuration of the cloud server 1A.

The cloud server 1A includes a CPU 101, a system controller 102, a main memory 103, a graphics processing unit (GPU) 104, a video memory (VRAM) 104A, a BIOS-ROM 105, an HDD 106, a LAN controller 107, an embedded controller/keyboard controller IC (EC/KBC) 108, a sound controller 109, an EEPROM 113, a keyboard 114, a pointing device 115, a speaker 116, a display (LCD) 117, etc. These components in the cloud server 1A are connected with each other through an internal bus.

The CPU 101 is a processor for controlling an operation of various components in the cloud server 1A. The CPU 101 executes various types of software loaded from the HDD 106 which is a storage device into the main memory 103. The software includes an operating system (OS) 111 and various application programs. The application programs include, for example, a monitoring server program 112. The monitoring server program 112 is a program for managing operation data, etc., of various home electrical appliances 2A, 2B and 2C used by the monitored user, and providing the client 3A used by the monitoring user with monitoring data based on the operation data, etc.

The CPU 101 includes a memory controller which access-controls the main memory 103. In addition, the CPU 101 executes a basic input/output system (BIOS) stored in the BIOS-ROM 105. The BIOS is a program for hardware control.

A GPU 104 is a display controller for controlling the LCD 117 used as a display of a computer. A display signal generated by the GPU 104 is transmitted to the LCD 117.

The system controller 102 is a device for connecting between a local bus of the CPU 101 and various components. In addition, the system controller 102 has a function of communicating with various components via a serial bus of, e.g. PCI EXPRESS or USB.

The sound controller 109 is a sound source device, and outputs audio data to be played to the speaker 116. The LAN controller 107 is a device configured to execute, for example, wired communication of the Ethernet™ or wireless communication of the IEEE 802.11.

The EC/KBC 108 is a one-chip microcomputer in which an embedded controller for power control and a keyboard controller for controlling the keyboard (KB) 114, the pointing device 115, etc., are integrated. The EC/KBC 108 has a function of powering on or off the cloud server 1A in accordance with the user's operation of a power button.

FIG. 5 illustrates an example of the system configuration of the client 3A used by the monitoring user. Suppose the client 3A is realized as a digital television receiver.

The client (digital television receiver) 3A includes a controller 201, a tuner 203, a demodulator 204, a signal processor 205, a graphics processor 206, an OSD signal generator 207, a video processor 208, a display (LCD) 209, an audio processor 210, a speaker 211, a remote control signal receiver 216, a LAN controller 218, etc. The digital television receiver 3A may further include a camera module 219 and a microphone 220.

The controller 201 controls an operation of each component in the digital television receiver 3A. The controller 201 includes a CPU 215, a ROM 212, a RAM 213, and a nonvolatile memory 214. The ROM 212 stores a control program executed by the CPU 215. The nonvolatile memory 214 stores various types of setting information and control information. The CPU 215 loads instructions and data required for processing into the RAM 213, and performs the processing. The CPU 215 executes, for example, a monitoring client program 213A loaded into the RAM 213. For example, the monitoring client program 213A has a function of receiving monitoring data from the cloud server 1A, and indicating information based on the monitoring data to a user.

A broadcast signal receiving antenna 202 receives a digital television broadcast signal (for example, a terrestrial digital television broadcast signal, a satellite digital television broadcast signal, etc.). The broadcast signal receiving antenna 202 outputs the received digital television broadcast signal to the tuner 203 through an input terminal. The tuner 203 tunes a broadcast signal of a channel selected by a user from this broadcast signal. The tuner 203 outputs the tuned broadcast signal to the demodulator 204 (for example, an orthogonal frequency division multiplexing (OFDM) demodulator, a phase shift keying (PSK) modulator, etc.). The demodulator 204 demodulates the broadcast signal tuned by the tuner 203 to a digital video signal and a digital audio signal. The demodulator 204 outputs the demodulated digital video signal and audio signal to the signal processor 205.

The signal processor 205 performs predetermined digital signal processing on the digital video signal and audio signal output from the demodulator 204. The signal processor 205 outputs the video signal and audio signal on which the predetermined digital signal processing is performed to the graphics processor 206 and the audio processor 210.

The audio processor 210 converts the input digital audio signal into an analog audio signal which can be played by the speaker 211. The audio processor 210 outputs the analog audio signal to the speaker 211. The speaker 211 plays audio based on the input analog audio signal.

The graphics processor 206 superimposes an on-screen display (OSD) signal such as a menu generated by an OSD signal generator 207 on the digital video signal output from the signal processor 205. The OSD signal generator 207 generates the OSD signal for displaying information based on the monitoring data. The graphics processor 206 outputs the video signal on which the OSD signal is superimposed to the video processor 208. The graphics processor 206 may output either the video signal which is an output of the signal processor 205 or the OSD signal which is an output of the OSD signal generator 207 to the video processor 208.

The video processor 208 performs predetermined processing on the input digital video signal. The predetermined processing includes, for example, processing for sharpening the input digital video signal. The video processor 208 converts the digital video signal on which the predetermined processing is performed into an analog video signal which can be displayed on the display 209. The video processor 208 outputs the analog video signal to the display 209. The display 209 displays video based on the input analog video signal.

The LAN controller 218 is a device configured to execute, for example, wired communications conforming to the Ethernet standard, wireless communications conforming to the IEEE 802.11 standard, etc.

The remote control signal receiver 216 receives a remote control signal (for example, a signal of infrared rays) transmitted from a remote controller 217. The remote control signal receiver 216 outputs the received remote control signal to the controller 201. The remote control signal receiver 216 receives, for example, a remote control signal indicating a shift from a normal mode to a monitoring mode, or that indicating a shift from the monitoring mode to the normal mode. The monitoring client program 213A executed on the CPU 215 in the controller 201 performs processing for switching, for example, the EPG 60A displayed in the normal mode and the EPG 60B displayed in the monitoring mode in accordance with the remote control signal.

It should be noted that the client 3A may be an electronic apparatus (for example, a personal computer) lacking a structure of receiving a television broadcast signal (i.e., the tuner 203, etc.). For example, the client 3A can also display a program using program data (content data) received from a server on the Internet.

In addition, the television receiver 2A used by the monitored user may have a system configuration similar to that of the client 3A used by the monitoring user. The television receiver 2A may further include the camera module 219 and the microphone 220. Since the camera module 219 is, for example, a subminiature camera (pinhole camera), an image of the monitored user can be obtained without letting the user be conscious. The microphone 220 is used, for example, for a conversation between the monitored and monitoring users, or between the monitored user and an avatar.

Next, a first example of the functional configuration of the monitoring server program 112 executed on the cloud server 1A will be described with reference to FIG. 6. As described above, the monitoring server program 112 manages operation data, etc., of various home electrical appliances 2A, 2B and 2C used by the monitored user (first user), and provide the client 3A used by the monitoring user (second user) with the monitoring data based on the operation data, etc. The monitoring server program 112 includes, for example, a receiver 151, a sleeping time estimator 152, a pattern estimator 153, and a transmitter 154.

The receiver 151 collects data from the various home electrical appliances used by the monitored user. More specifically, the receiver 151 receives operation data and viewing data transmitted from a transmitter 252 in the TV 2A. The operation data of the TV 2A includes an operating period during which a program is viewed on the TV 2A (for example, from 06:00 to 08:00). The viewing data of the TV 2A includes a date and time of broadcast, a title, a channel, a category (genre), etc., of the program viewed by the monitored user. The viewing data is generated by a viewing data generator 251 in the TV 2A, for example, when the program is viewed by the monitored user.

In addition, the receiver 151 receives operation data transmitted from a transmitter 261 in the lighting fixture 2B. The operation data of the lighting fixture 2B includes the operating period during which the lighting fixture 2B is turned on (for example, from 06:00 to 22:00). Further, the receiver 151 receives operation data and temperature and humidity data transmitted from a transmitter 273 in the air conditioner 2C. The operation data of the air conditioner 2C includes an operating period during which the air conditioner 2C is used (for example, from 10:00 to 20:00). The temperature and humidity data of the air conditioner 2C includes a temperature and a humidity detected, for example, for each predetermined time by a temperature sensor 271 and a humidity sensor 272 in the air conditioner 2C.

Then, the receiver 151 stores the received operation data of the TV 2A, the received operation data of the lighting fixture 2B, and the received operation data and temperature and humidity data of the air conditioner 2C in a storage medium, etc. The receiver 151 also stores the received viewing data in the TV viewing history database 1B.

FIG. 7 illustrates a configuration example of operation data of home electrical appliances used by the cloud server 1A. The cloud server 1A can handle operation data transmitted from home electrical appliances used by each of a plurality of monitored users. The operation data includes a plurality of entries generated using the operation data transmitted from the home electrical appliances used by the monitored user. Each entry includes, for example, a user ID, a date, a lighting operating period, an air conditioner operating period, a temperature, a humidity, and a TV operating period. Suppose the entry is generated for each monitored user everyday for ease of description.

In a monitored user's entry corresponding to a certain date, "user ID" indicates identification information of the user. "Date" indicates the date. "Lighting operating period" indicates an operating period of the lighting fixture 2B used by the user on that date. "Air conditioner operating period" indicates an operating period of the air conditioner 2C used by the user on that date. "Temperature" indicates the temperature detected by the air conditioner 2C used by the user on that date (i.e., a temperature of a room of the monitored user). "Humidity" indicates the humidity detected by the air conditioner 2C used by the user on that date (i.e., the humidity of the room of the monitored user). "TV operating period" indicates the operating period of the TV 2A used by the user on that date.

In addition, FIG. 8 illustrates a configuration example of the viewing data used by the cloud server 1A. The viewing data includes a plurality of entries corresponding to a plurality of programs viewed by the monitored user. Each entry includes, for example, user ID, date, time, channel, program title, viewing status, category, degree of smile, and biorhythm.

In an entry corresponding to a certain program, "user ID" indicates identification information of the user who watched the program (monitored user). "Date" indicates the date on which the program is broadcast. "Time" indicates the time at which the program is broadcast. "Channel" indicates the channel on which the program is broadcast. "Program title" indicates the title of the program. "Viewing status" indicates the viewing status of the program, and, for example, "viewed," "recorded (unviewed)," "reserved to be recorded," etc., may be set. "Category" indicates the category (genre) of the program, and, for example, "news," "comedy," "education," "documentary," "animation," etc., may be set. "Degree of smile" indicates how much the user smiled when viewing the program. The degree of smile may indicate how often the user smiled when viewing the program. "Biorhythm" indicates the biorhythm of the user when viewing the program. It should be noted that a value calculated by, for example, the monitoring server program 112 and corresponding to the program is set for the degree of smile and the biorhythm.

Next, the sleeping time estimator 152 and the pattern estimator 153 generates monitoring data concerning the monitored user at predetermined intervals (for example, everyday) or in response to a request from the client 3A used by the monitoring user. More specifically, the sleeping time estimator 152 estimates a sleep period of the monitored user using the operation data of the home electrical appliance 2A, 2B, 2C used by the monitored user. The sleeping time estimator 152 estimates the sleep period (i.e., asleep or awake) of the monitored user based on the fact, for example, that a user is likely to be awake when the home electrical appliance 2A, 2B, 2C are operated (i.e., turned on), and the user is likely to be asleep when the home electrical appliance 2A, 2B, 2C is not operated (i.e., turned off).

Then, the pattern estimator 153 estimates a living pattern of the monitored user using the estimated sleep period of the monitored user and the viewing data stored in the TV viewing history database 1B. The used viewing data is data indicating, for example, a program viewed or recorded by the monitored user in the past, a program currently being viewed by the monitored user, etc. The pattern estimator 153 detects a first program frequently viewed by the monitored user during the current period as a living pattern of the monitored user using the viewing data. More specifically, if the current period is, for example, at 8 p.m. on Sunday, the pattern estimator 153 detects a program named "XXX" frequently viewed by the monitored user at 8 p.m. on Sunday as a living pattern of the monitored user, using past viewing data corresponding to 8 p.m. of Sunday.

The pattern estimator 153 generates monitoring data (living pattern data) indicating the estimated living pattern and the current status of the monitored user (for example, a currently-viewed program, asleep or awake, etc.). The living pattern data includes data indicating, for example, the sleep period of the monitored user, the first program frequently viewed by the monitored user during the current period, and the program currently being viewed by the monitored user.

The transmitter 154 transmits the generated monitoring data (living pattern data) to the client 3A used by the monitoring user.

In the client 3A used by the monitoring user, the monitoring client program 213A configured to receive the monitoring data from the cloud server 1A and to indicate information based on the monitoring data to the user is executed. The monitoring client program 213A includes, for example, an EPG data receiver 311, an EPG generator 312, a monitoring data receiver 313, a monitoring information generator 314, and a display processor 315. Suppose the client 3A is set to either the monitoring mode in which information concerning the monitored user is displayed, or the normal mode in which the information concerning the monitored user is not displayed.

First, the EPG data receiver 311 receives EPG data. The EPG data receiver 311 may receive EPG data included in a television broadcast signal through the antenna 202, etc., or receive EPG data from the TV viewing history database 1B through the network 4. The EPG generator 312 generates an EPG using the received EPG data, that is, generates data for displaying the EPG on a screen of the display 209.

Next, the monitoring data receiver 313 receives monitoring data from the cloud server 1A (transmitter 154). The monitoring data receiver 313 receives the monitoring data, for example, when the client 3A is set to the monitoring mode.

The monitoring information generator 314 superimposes information of the monitored user on the EPG generated by the EPG generator 312 using the received monitoring data. The information of the monitored user includes, for example, a program currently being viewed by the monitored user, a program frequently viewed by the monitored user (program frequently viewed in the past), whether the monitored user is asleep or awake, etc. The monitoring information generator 314 displays the program being viewed and frequently viewed by the monitored user to be identified, for example, by changing a color or a design of an area, a closing line surrounding the area on an EPG corresponding to the program, etc., or by drawing a predetermined mark (image) in the area. Also, the monitoring information generator 314 displays an area indicating a time on the EPG using the color, design, closing line, etc., such that a period during which the monitored user is awake and a period during which the monitored user is asleep can be distinguished.

As shown in FIG. 3, the display processor 315 displays the EPG 60B on which the information of the monitored user is superimposed on a screen, when the client 3A is in the monitoring mode. In the meantime, when the client 3A is in the normal mode, the display processor 315 displays the EPG 60A on the screen.

Figure 9:
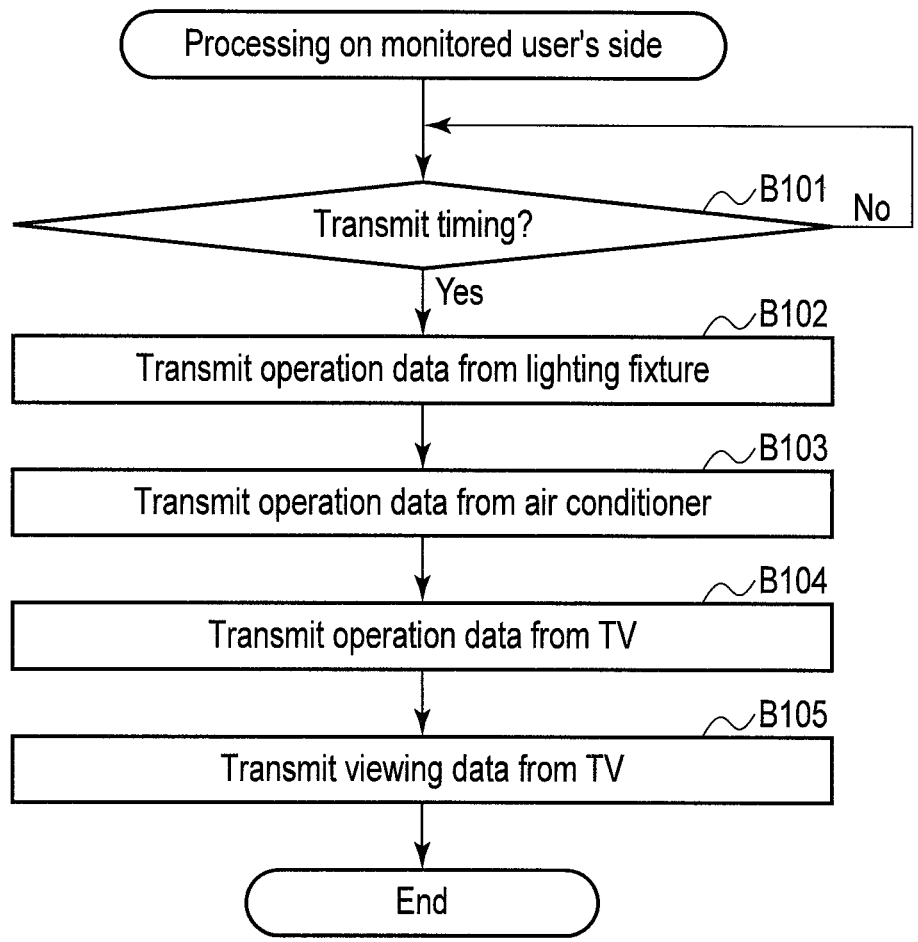
FIG. 9 is a flowchart illustrating an example of the procedure of a process executed by the electronic apparatuses (home electrical appliances) used by the monitored user of FIG. 2.
Figure 11:
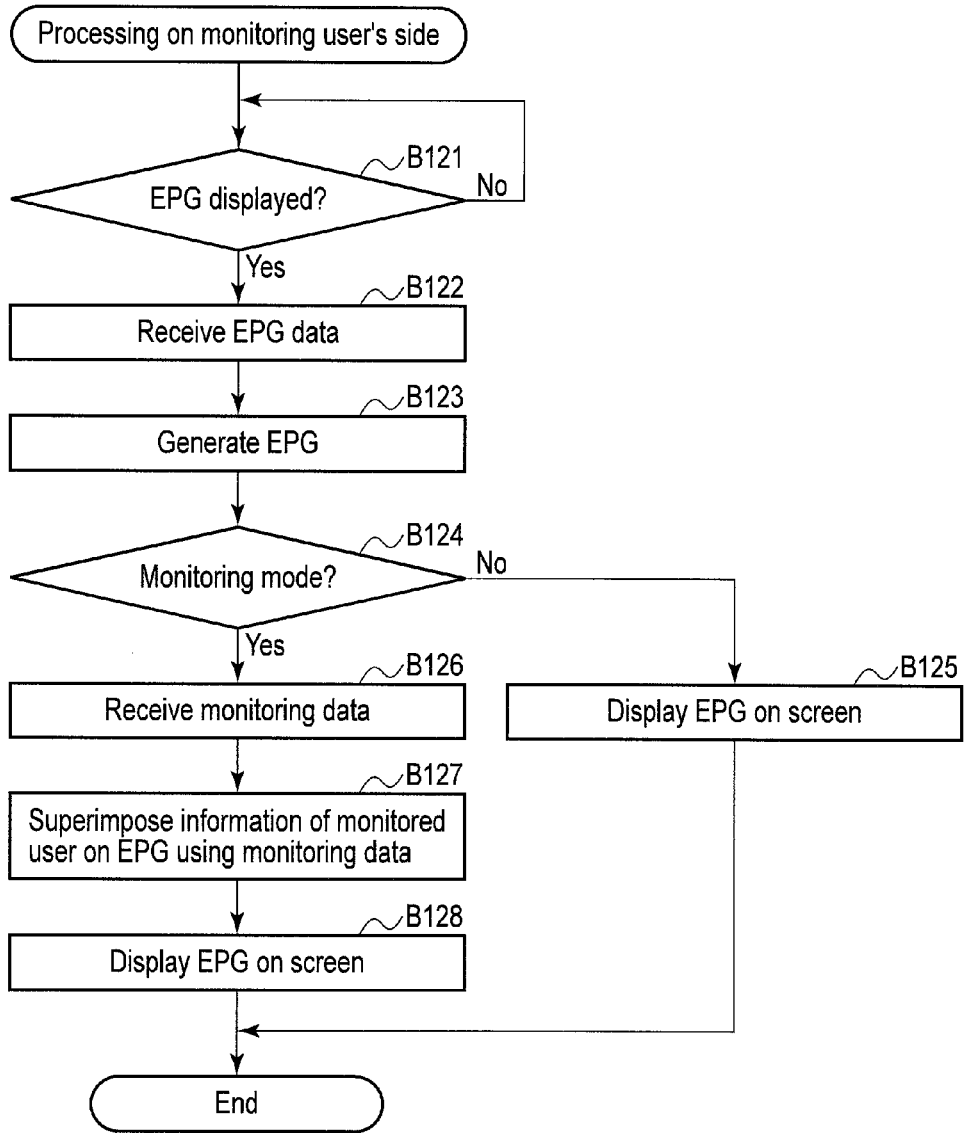
FIG. 11 is a flowchart illustrating an example of the procedure of a process executed by the electronic apparatus (TV) used by the monitoring user of FIG. 2.

Processing when data indicating a living pattern of the monitored user is transmitted from the cloud server 1A to the client 3A used by the monitoring user will be described with reference to FIGS. 9 to 11.

First, the processing procedure on the side of the monitored user will be described with reference to the flowchart of FIG. 9.

First, the home electrical appliance 2A, 2B, 2C used by the monitored user determines whether data should be transmitted at this time or not (block B101). If the data should not be transmitted at this time (No in block B101), the procedure returns to block B101, and whether the data should be transmitted at this time or not is determined again.

If the data should be transmitted at this time (Yes in block B101), the transmitter 261 of the lighting fixture 2B transmits operation data to the cloud server 1A (block B102). The transmitter 273 of the air conditioner 2C transmits the operation data to the cloud server 1A (block B103). The transmitter 252 of the TV 2A transmits the operation data to the cloud server 1A (block B104). Also, the transmitter 252 of the TV 2A transmits viewing data to the cloud server 1A (block B105).

The flowchart of FIG. 10 illustrates the procedure of monitoring processing by the cloud server 1A.

The receiver 151 of the cloud server 1A receives the viewing data of the TV 2A used by the monitored user (block B111). The receiver 151 stores the received viewing data of the TV 2A in the TV viewing history database 1B (block B112). In addition, the receiver 151 receives the operation data of the home electrical appliance used by the monitored user, that is, the operation data of the TV 2A, the lighting fixture 2B and the air conditioner 2C (block B113), and stores the operation data in a storage medium, etc. (block B114).

Next, the sleeping time estimator 152 determines whether transmission of monitoring data is requested by the client 3A used by the monitoring user or not (block B115). If the transmission of the monitoring data is not requested (No in block B115), the procedure returns to block B111, and the processing, etc., of receiving data from the home electrical appliances 2A, 2B and 2C used by the monitored user continues.

If the transmission of the monitoring data is requested (Yes in block B115), the sleeping time estimator 152 estimates a sleep period of the monitored user using the stored operation data of the home electrical appliance 2A, 2B, 2C (block B116). The pattern estimator 153 estimates a living pattern of the monitored user using the estimated sleep period of the monitored user and the viewing data stored in the TV viewing history database 1B (block B117). Then, the transmitter 154 transmits the monitoring data indicating the estimated living pattern and the current status of the monitored user (for example, whether the monitored user is asleep or awake, a program being viewed, etc.) to the client 3A used by the monitoring user (block B118).

Next, the procedure of display control processing by the client 3A on the side of the monitoring user will be described with reference to the flowchart of FIG. 11.

First, the EPG data receiver 311 determines whether to display an EPG or not (block B121). If the EPG is not displayed (No in block B121), the procedure returns to block B121, and whether to display the EPG or not is determined again.

If the EPG is displayed (Yes in block B121), the EPG data receiver 311 receives EPG data (block B122). Then, the EPG generator 312 generates data for displaying the EPG on a screen using the received EPG data (block B123).

Next, the monitoring data receiver 313 determines whether the client 3A is in the monitoring mode or not (block B124).

If the client 3A is not in the monitoring mode (No in block B124), the display processor 315 displays the EPG on the screen using the data generated by the EPG generator 312 (block B125).

If the client 3A is in the monitoring mode (Yes in block B124), the monitoring data receiver 313 receives the monitoring data from the cloud server 1A (block B126). The monitoring information generator 314 superimposes information of the monitored user (a program being viewed, a program frequently viewed in the past, whether the monitored user is asleep or awake, etc.) on the EPG using the received monitoring data (block B127). Then, the display processor 315 displays the EPG on which the information of the monitored user is superimposed on the screen (block B128).

When information for monitoring a user is provided, the above structures allow a burden imposed on the monitored and monitoring users to be reduced.

Next, FIG. 12 illustrates a case where the cloud server 1A indicates the biorhythm of the monitored user (elderly person) to the monitoring user (family). The home electrical appliance 2A, 2B used by the monitored user transmits operation data, etc., to the cloud server 1A through the network 4.

More specifically, the lighting fixture 2B transmits lighting operation data indicating the operating period based on the on/off state of the lighting fixture 2B to the cloud server 1A. The television receiver (TV) 2A transmits TV operation data indicating the operating period based on the on/off state of the TV 2A to the cloud server 1A. Also, the TV 2A stores the viewing data indicating a program viewed by the monitored user to the TV viewing history database 1B through the network 4. The TV viewing history database 1B accumulates, for example, the electronic program guide (EPG) data and the viewing data of the monitored user in a given period. The cloud server 1A can receive the viewing data indicating the program viewed by the monitored user from the TV viewing history database 1B by accessing the TV viewing history database 1B through the network 4.

Further, the TV 2A generates images including face images of the monitored user using a camera 219 connected to or embedded in the TV 2A. The TV 2A generates the face images of a user viewing a program displayed on a screen. The TV 2A detects the face images from the generated images, and then calculates a degree of smile indicating to what extent the face images show smiling. Also, the TV 2A calculates the degree of smile corresponding to each of the images, and calculates a frequency of smile using the result by continuously analyzing the images including the face images of the monitored user. Then, the TV 2A transmit smile data including the calculated degree of smile and frequency of smile to the cloud server 1A.

Since the TV 2A used by the monitored user transmits not image data but metadata such as the smile data obtained from the images to the cloud server 1A, privacy of the monitored user can be protected.

The cloud server 1A estimates the biorhythm of the monitored user using the received data. The biorhythm is indicated by, for example, a value representing whether the monitored user is in good health or not. The cloud server 1A transmits the data indicating the estimated biorhythm of the monitored user to the client 3A used by the monitoring user through the network 4.

FIG. 13 illustrates a case where the client 3A displays the biorhythm of the monitored user.

The client 3A displays an area (window) 65 including a graph 67 indicating a change in biorhythm, for example, in an area of at least part of a screen of the client 3A using the data of the biorhythm transmitted from the cloud server 1A. The client 3A may display only the area 65 on the screen, or superimpose the area 65 on video being viewed or an EPG to display it on the screen. The normal range 68 of a value of the biorhythm may be indicated on the graph 67. Lines indicating the normal range 68 are drawn on the graph 67 shown in FIG. 13. The normal range 68 is set by analyzing, for example, past data on the biorhythm of the monitored user or data on the biorhythm of a number of users.

The user using the client 3A (monitoring user) can confirm whether the monitored user is in good health or not (how well the user is) by viewing the graph 67. Since the monitoring user can recognize that the monitored user is unwell, for example, when a value 66 indicated by the graph 67 is outside the normal range 68, the monitoring user is urged to visit the monitored user's house, to telephone the monitored user, etc.

Figure 14:
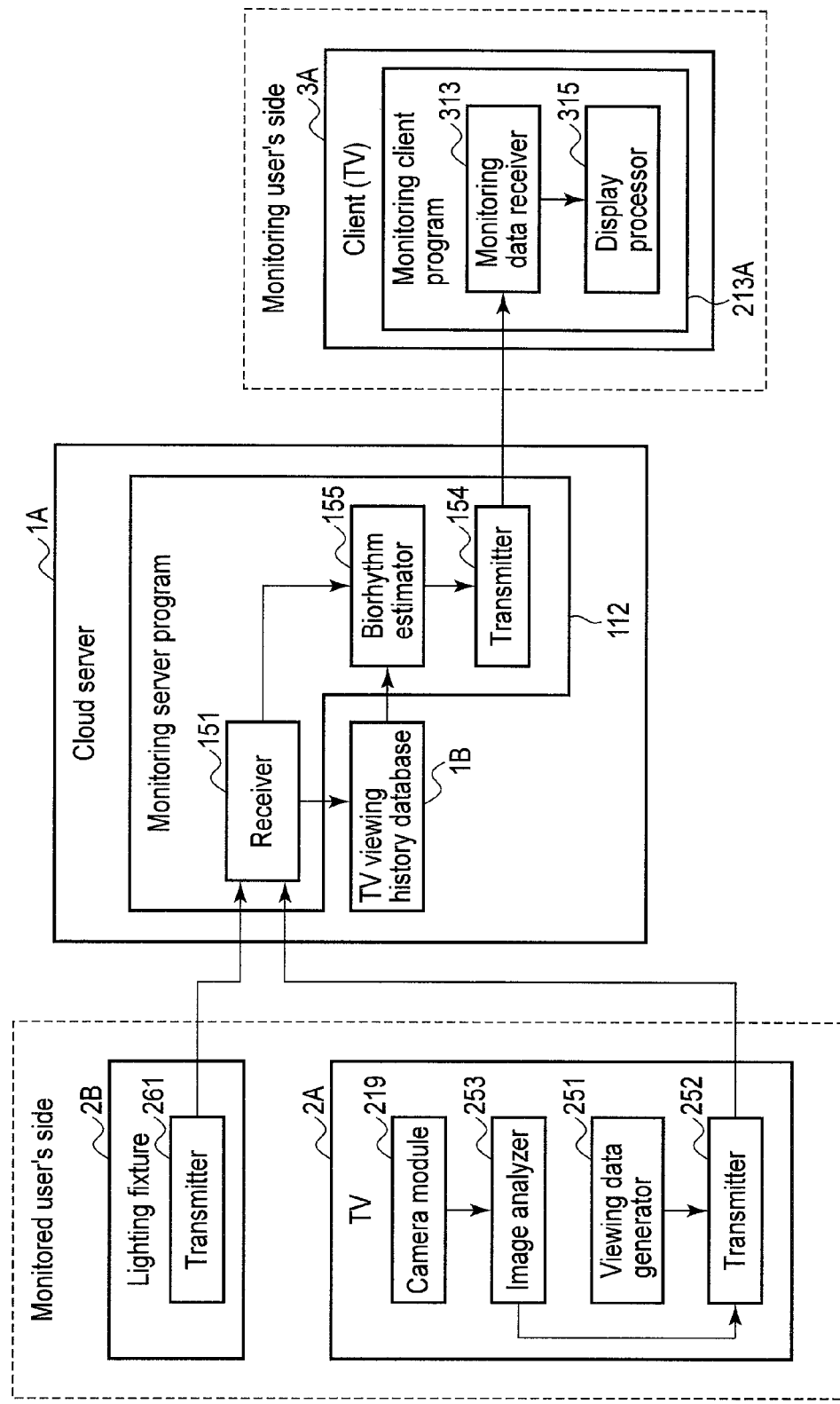
FIG. 14 is a block diagram illustrating a second example of the functional configuration of the electronic apparatus according to the embodiment.

A second example of the functional configuration of the monitoring server program 112 executed on the cloud server 1A will be described with reference to FIG. 14. The monitoring server program 112 includes, for example, the receiver 151, the transmitter 154 and a biorhythm estimator 155.

The receiver 151 receives data from various home electrical appliances used by the monitored user. More specifically, the receiver 151 receives the smile data and viewing data transmitted from the transmitter 252 in the TV 2A. The smile data of the TV 2A includes, for example, the degree of smile and the frequency of smile when the monitored user views a program on the TV 2A. An image analyzer 253 in the TV 2A calculates the degree and frequency of smile in the face images of the monitored user by analyzing images that are captured by the camera module 219. Also, the viewing data of the TV 2A includes a date and time of broadcast, a title, a channel, a category (genre), etc., of the program viewed by the monitored user. The viewing data is generated by the viewing data generator 251 in the TV 2A, for example, in accordance with a program viewed by the monitored user.

In addition, the receiver 151 receives operation data transmitted from the transmitter 261 in the lighting fixture 2B. The operation data of the lighting fixture 2B includes an operating period (for example, from 06:00 to 22:00) of the lighting fixture 2B. Then, the receiver 151 stores the received operation data of the lighting fixture 2B in a storage medium, etc. The receiver 151 also stores the received smile data and viewing data of the TV 2A in the TV viewing history database 1B. The structure of viewing data stored in the TV viewing history database 1B is similar to that shown in FIG. 8.

Next, the biorhythm estimator 155 generates monitoring data concerning the monitored user at predetermined intervals (for example, everyday) or in response to a request of the client 3A used by the monitoring user. More specifically, the biorhythm estimator 155 estimates the biorhythm of the monitored user using the operation data of the lighting fixture 2B used by the monitored user and the viewing data and smile data stored in the TV viewing history database 1B. The biorhythm estimator 155 calculates a degree indicating whether the user is well or not as the biorhythm of the monitored user, for example, based on whether or not a lighting fixture is appropriately used (for example, whether or not there is a time in which the lighting fixture is not used even when it is dark), whether or not a degree of smile or a frequency of smile is high when the category of the viewed program is a comedy, etc.

The transmitter 154 transmits the estimated monitoring data indicating the biorhythm to the client 3A used by the monitoring user.

In the client 3A used by the monitoring user, the monitoring client program 213A configured to receive the monitoring data from the cloud server 1A and to indicate information based on the monitoring data to a user is executed. The monitoring client program 213A includes, for example, the monitoring data receiver 313 and the display processor 315.

The monitoring data receiver 313 receives the monitoring data from the cloud server 1A (transmitter 154).

Then, the display processor 315 displays the biorhythm 67 of the monitored user on a screen using the monitoring data, as shown in FIG. 13. When the client 3A is a TV, the display processor 315 displays the biorhythm 67 on the screen, for example, in response to the selection of a dedicated channel for displaying the biorhythm, or in accordance with the press of a dedicated button provided in the remote controller 217 or in a main body of the client 3A.

The display processor 315 may draw lines, etc., indicating the normal range 68 of the biorhythm on this screen. In addition, the display processor 315 can indicate that the current value 66 of the biorhythm is abnormal, when the current value 66 of the biorhythm is outside the normal range 68. The display processor 315 indicates the abnormal value of the biorhythm by, for example, a color, a mark, etc. It should be noted that the abnormal value of the biorhythm can be indicated by audio or an alarm.

Figure 15:
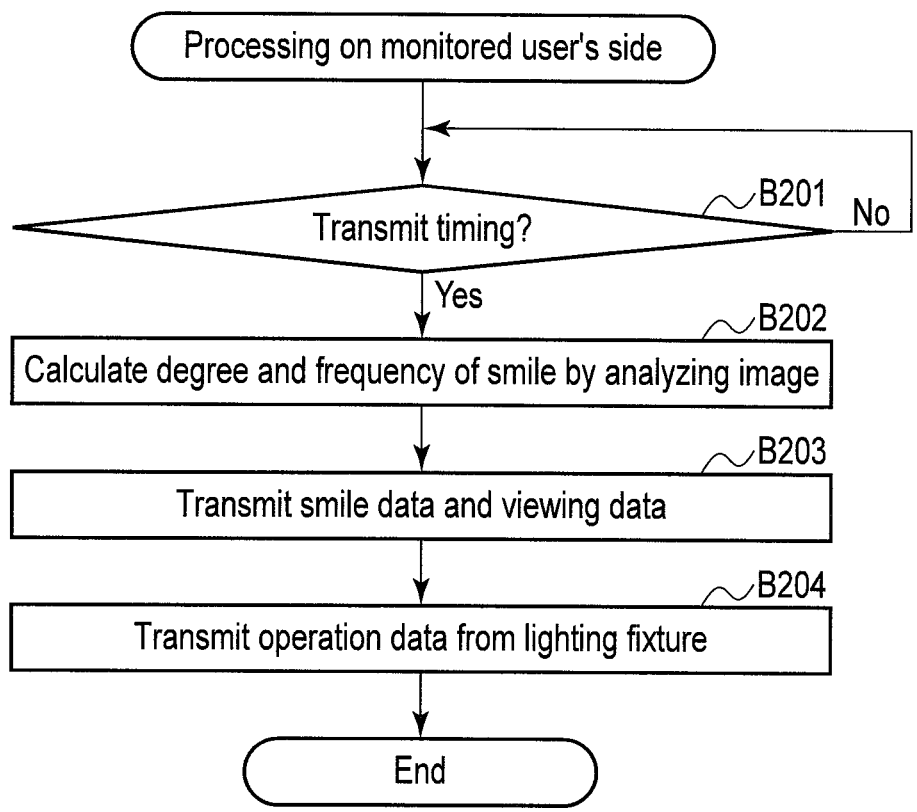
FIG. 15 is a flowchart illustrating an example of the procedure of a process executed by the electronic apparatuses (home electrical appliances) used by the monitored user of FIG. 12.

Processing when data indicating the biorhythm of the monitored user is transmitted from the cloud server 1A to the client 3A used by the monitoring user will be described with reference to FIGS. 15 to 17.

First, the procedure of processing on the side of the monitored user will be described with reference to the flowchart of FIG. 15.

First, home electrical appliance 2A, 2B used by the monitored user determines whether data should be transmitted at this time or not (block B201). If the data should not be transmitted at this time (No in block B201), the procedure returns to block B201, and whether the data should be transmitted at this time or not is determined again.

If the data should be transmitted at this time (Yes in block B201), the image analyzer 253 of the TV 2A calculates a degree of smile and a frequency of smile of the face images of the monitored user by analyzing images captured by the camera module 219 (block B202). Then, the transmitter 252 of the TV 2A transmits smile data including the calculated degree and frequency of smile and the viewing data of the TV 2A to the cloud server 1A (block B203). In addition, the transmitter 261 of the lighting fixture 2B transmits the operation data to the cloud server 1A (block B204).

Figure 16:
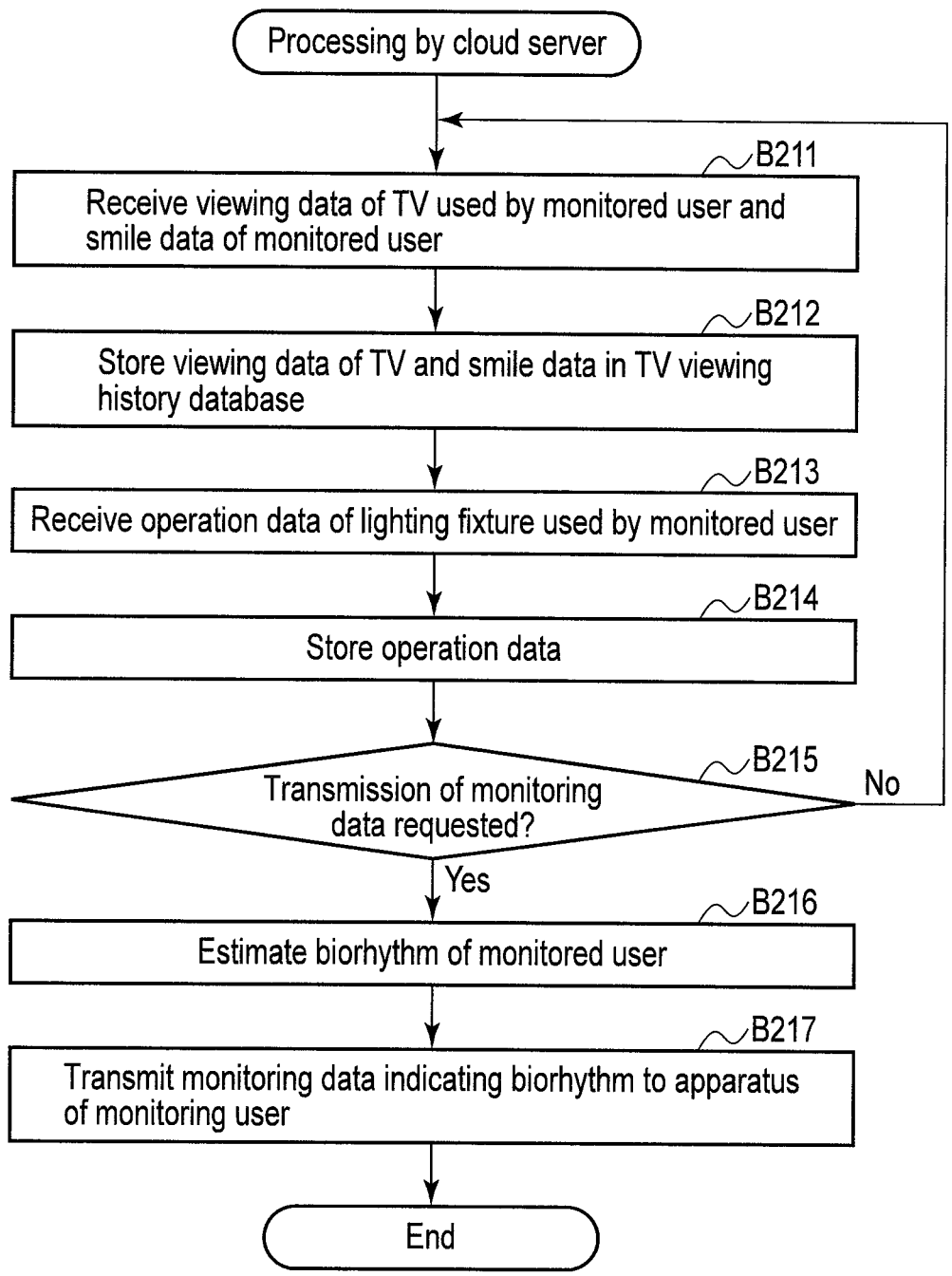
FIG. 16 is a flowchart illustrating the second example of the procedure of a process executed by the electronic apparatus according to the embodiment.
Figure 17:
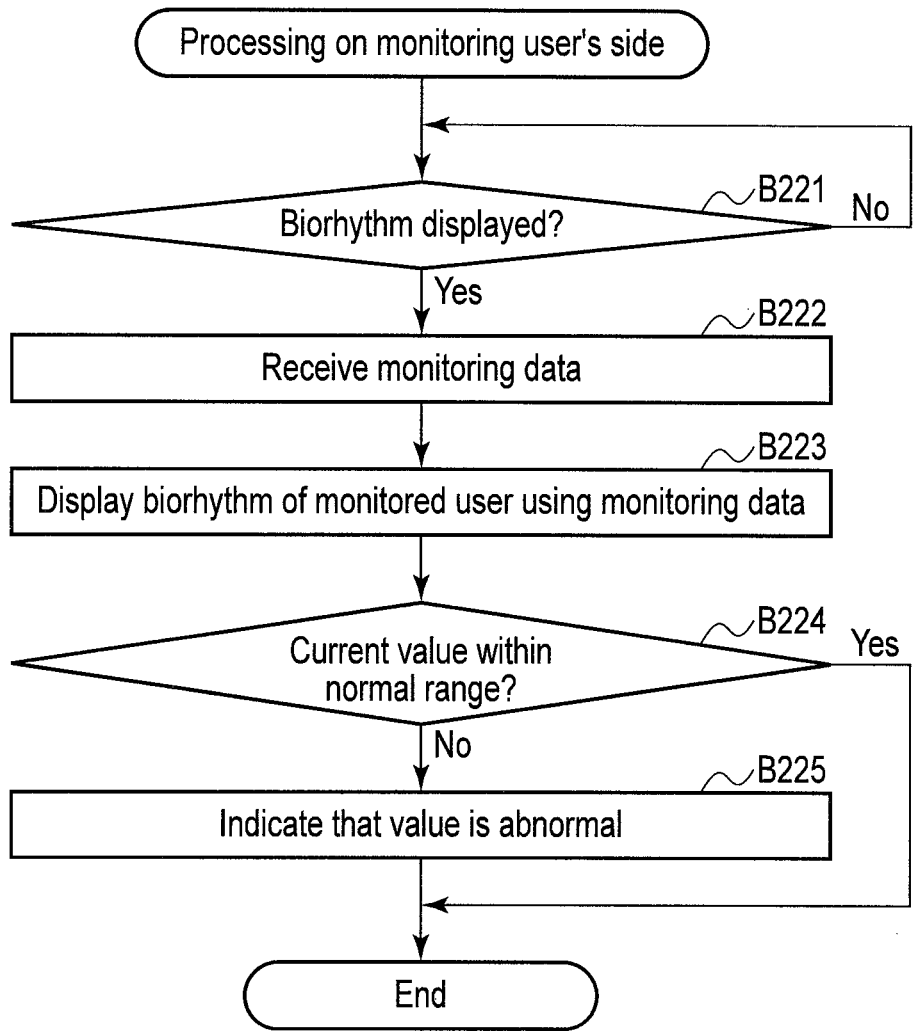
FIG. 17 is a flowchart illustrating an example of the procedure of a process executed by the electronic apparatus (TV) used by the monitoring user of FIG. 12.

The flowchart of FIG. 16 illustrates the procedure of monitoring processing by the cloud server 1A.

The receiver 151 of the cloud server 1A receives the viewing data of the TV 2A used by the monitored user and the smile data of the monitored user (block B211). The receiver 151 stores the received viewing data of the TV 2A and the received smile data in the TV viewing history database 1B (block B212). In addition, the receiver 151 receives the operation data of the lighting fixture 2B used by the monitored user (block B213). Then, the receiver 151 stores the received operation data in a storage medium, etc. (block B214).

Next, the biorhythm estimator 155 determines whether transmission of the monitoring data is requested by the client 3A used by the monitoring user or not (block B215). If the transmission of the monitoring data is not requested (No in block B215), the procedure returns to block B211, and the processing, etc., of receiving data from the home electrical appliance 2A, 2B used by the monitored user continues.

If the transmission of the monitoring data is requested (Yes in block B215), the biorhythm estimator 155 estimates the biorhythm of the monitored user using the stored operation data of the lighting fixture 2B and the viewing data and smile data stored in the TV viewing history database 1B (block B216). Then, the transmitter 154 transmits the monitoring data indicating the estimated biorhythm to the client 3A used by the monitoring user (block B217).

The procedure of display control processing on the side of the monitoring user by the client 3A will be described with reference to FIG. 17.

First, the monitoring data receiver 313 determines whether to display the biorhythm of the monitored user or not (block B221). If the biorhythm is not to be displayed (No in block B221), the procedure returns to block B221, and whether to display the biorhythm or not is determined again.

If the biorhythm is to be displayed (Yes in block B221), the monitoring data receiver 313 receives the monitoring data from the cloud server 1A (block B222). Then, the display processor 315 displays the biorhythm of the monitored user on a screen using the monitoring data (block B223).

Next, the display processor 315 determines whether the current value of the biorhythm is within the normal range or not (block B224). If the current value of the biorhythm is outside the normal range (No in block B224), the display processor 315 indicates that the current value of the biorhythm is the abnormal value (block B225). The display processor 315 indicates the abnormal value of the biorhythm, for example, by a color, a mark, etc. It should be noted that the abnormal value of the biorhythm may be indicated by audio.

If the current value of the biorhythm is within the normal range (Yes in block B224), the processing is terminated.

Next, FIG. 18 illustrates a case where information for supporting a conversation with the monitored user (elderly person) is indicated to the monitoring user (a specialist, a local community organization, etc.) by the cloud server 1A. The television receiver (TV) 2A used by the monitored user transmits the operation data, etc., to the cloud server 1A through the network 4.

More specifically, the TV 2A stores the viewing data, which indicates a program viewed by the monitored user, in the TV viewing history database 1B through the network 4. The TV viewing history database 1B accumulates, for example, the electronic program guide (EPG) data and the viewing data of the monitored user in a given period. The cloud server 1A can receive the viewing data indicating the program viewed by the monitored user from the TV viewing history database 1B by accessing the TV viewing history database 1B through the network 4.

The cloud server 1A provides a function for causing the monitored user to have a conversation with an avatar (for example, a virtual careworker, a virtual pet, etc.). The cloud server 1A selects an avatar appropriate for the monitored user from a plurality of avatars corresponding to various hobbies, tastes, interests, etc.

If conversation with the avatar is enabled, the cloud server 1A receives audio data based on utterances of the monitored user from the TV 2A, determines the utterances of the avatar in response to the utterances of the user by analyzing the received audio data, and transmits the audio data corresponding to the determined utterances to the TV 2A. The TV 2A receives the audio data representing the utterances of the avatar from the cloud server 1A, and outputs it from the speaker 211. The conversation between the monitored user and the avatar is performed in this manner.

The cloud server 1A detects a hobby, a taste, an interest, etc., of the monitored user by analyzing the contents of the conversation using the audio data of the conversation with the avatar. Thus, the cloud server 1A can select an appropriate avatar for the monitored user from a plurality of avatars using, for example, data of a past conversation between the monitored user and the avatars.

In addition, the cloud server 1A can provide a client such as a tablet computer 3B or a smartphone 3C used by the monitoring user with conversation support data for supporting a conversation with the monitored user, when the monitored and monitoring users have the conversation. It should be noted that the client used by the monitoring user may be a TV 3A, a cellular phone, a landline phone, etc.

The TV 2A used by the monitored user and the client 3B, 3C used by the monitoring user have a function of performing a conversation between users through the network 4 (hereinafter referred to also as a videophone function). The TV 2A and the client 3B, 3C transmit and receive the audio data or video data for the conversation through the network 4 in real time. The monitored user can have a conversation with a user belonging to a local community organization or a monitoring user such as a specialist using the videophone function.

For example, a camera and a microphone are provided in the tablet computer 3B or the smartphone 3C, and an application program (for example, Skype®) for transmitting and receiving the audio data or the video data in real time is installed on the tablet computer 3B or the smartphone 3C. The monitored user also uses a tablet computer, a smartphone, etc., instead of the TV 2A.

As described above, the cloud server 1A provides the client 3B, 3C used by the monitoring user with conversation support data for supporting the conversation with the monitored user when the monitored and monitoring users have a conversation. The client 3B, 3C displays, for example, information based on the conversation support data on a screen. The displayed information allows a user (monitoring user) belonging to, for example, a local community organization to talk with a topic which is likely to attract the monitored user's interest, allows a user sharing a hobby with the monitored user of a plurality of users belonging to the local community organization to be a conversation partner, etc. Also, the displayed information allows a specialist (monitoring user) to perform health support appropriate for the monitored user, to simply diagnose a disorder of the monitored user (for example, dementia) based on a conversation pattern included in the conversation support data, etc.

A third example of the functional configuration of the monitoring server program 112 executed on the cloud server 1A will be described with reference to FIG. 19. The monitoring server program 112 includes, for example, the receiver 151, the transmitter 154 and an interactive processor 156.

The receiver 151 receives data from the TV 2A used by the monitored user. More specifically, the receiver 151 receives viewing data transmitted from the transmitter 252 in the TV 2A. The viewing data includes a date and time of broadcast, a title, a channel, a category (genre), etc., of the program viewed by the monitored user. The viewing data is generated by the viewing data generator 251 in the TV 2A, for example, in accordance with the program viewed by the monitored user. The receiver 151 stores the received viewing data of the TV 2A in the TV viewing history database 1B. The configuration of the viewing data stored in the TV viewing history database 1B is similar to that shown in FIG. 8.

The interactive processor 156 performs processing for a conversation between the monitored user and the avatar, or between the monitored and monitoring users. The interactive processor 156 includes, for example, an avatar controller (conversation processor) 157, a voice recognition and pattern analyzer 158 and a conversation support data generator 160.

The avatar controller 157 and the voice recognition and pattern analyzer 158 perform the processing for the conversation between the monitored user and the avatar. The voice recognition and pattern analyzer 158 analyzes the audio data of the past conversation between the monitored user and the avatar (history of the conversation) to detect the conversation pattern. The voice recognition and pattern analyzer 158 performs, for example, voice recognition processing on the audio data of the conversation to generate text corresponding to the conversation and to detect the conversation pattern based on words, a pattern thereof appearing in the text (for example, co-occurrence probability of a word), etc.

The avatar controller (conversation processor) 157 selects an avatar for supporting the conversation with the monitored user, based on the conversation pattern and viewing data of the monitored user. The avatar controller 157 selects an avatar for providing a topic which, for example, is likely to attract the monitored user's interest (i.e., a topic by which a conversation may be continued) using the conversation pattern and viewing data of the monitored user from a plurality of avatars each providing different topics. The avatar controller 157 may select an avatar for providing a topic relevant to a program currently being viewed by the monitored user. Furthermore, the avatar controller 157 may transmit an image corresponding to the selected avatar to the client (TV) 2A of the monitored user and display the image on the screen of the client 2A.

The avatar controller 157 performs conversation processing with the monitored user using the selected avatar. The avatar controller 157 executes, for example, a program module corresponding to the selected avatar to perform the conversation processing. The avatar controller 157 receives the audio data based on utterances of the monitored user from a conversation processor 255 in the TV 2A used by the monitored user. The voice recognition and pattern analyzer 158 performs the voice recognition processing on the received audio data to generate corresponding text. Then, the avatar controller 157 generates reply audio data (audio data of the avatar) appropriate for the monitored user based on the generated text, a past conversation pattern, etc., and transmits the audio data to the conversation processor 255 of the TV 2A.

The conversation processor 255 of the TV 2A receives the audio data of the avatar from the cloud server 1A, and outputs the audio based on the received audio data using, for example, the speaker 211. This allows the monitored user and the avatar to have a conversation.

In addition, the voice recognition and pattern analyzer 158 and the conversation support data generator 160 perform processing for the conversation between the monitored and monitoring users. The voice recognition and pattern analyzer 158 and the conversation support data generator 160 generates conversation support data concerning the monitored user at predetermined intervals (for example, everyday) or in response to a request of the client 3B, 3C used by the monitoring user. More specifically, the voice recognition and pattern analyzer 158 analyzes the audio data of a past conversation between the monitored user and the avatar to detect the conversation pattern. The conversation support data generator 160 generates the conversation support data based on the conversation pattern and the viewing data. The conversation support data includes, for example, information indicating a hobby, a taste, an interest, etc. of the monitored user and information indicating a program viewed by the monitored user.

The transmitter 154 transmits the generated conversation support data to the client 3B, 3C used by the monitoring user.

In the client 3B, 3C used by the monitoring user, the monitoring client program 213A configured to receive the conversation support data from the cloud server 1A and to indicate the information based on the conversation support data to a user is executed. The monitoring client program 213A includes, for example, the monitoring data receiver 313 and the display processor 315.

The monitoring data receiver 313 receives the conversation support data from the cloud server 1A (transmitter 154).

Then, the display processor 315 displays information for supporting the conversation with the monitored user on a screen using the conversation support data. The information indicates, for example, information concerning a hobby, a taste, an interest, etc. of the monitored user and a program being viewed by the monitored user (for example, a title and contents of a program). It should be noted that the information may indicate text data concerning descriptions of a specific conversation, i.e., as to how the user responded to a certain talk, or the conversation pattern.

A conversation processor 316 of the client 3B, 3C and the conversation processor 255 of the TV 2A perform conversation processing for the monitoring user and the monitored user. That is, the conversation processor 316 of the client 3B, 3C transmit the audio data based on utterances of the monitoring user to the TV 2A through the network 4, and the conversation processor 255 of the TV 2A receives the audio data. Also, the conversation processor 255 of the TV 2A transmits the audio data based on utterances of the monitored user to the client 3B, 3C through the network 4, and the conversation processor 316 of the client 3B, 3C receives the audio data. In each of the client 3B, 3C and the TV 2A, audio based on the received audio data is output using, for example, the speaker 211.

Figure 20:
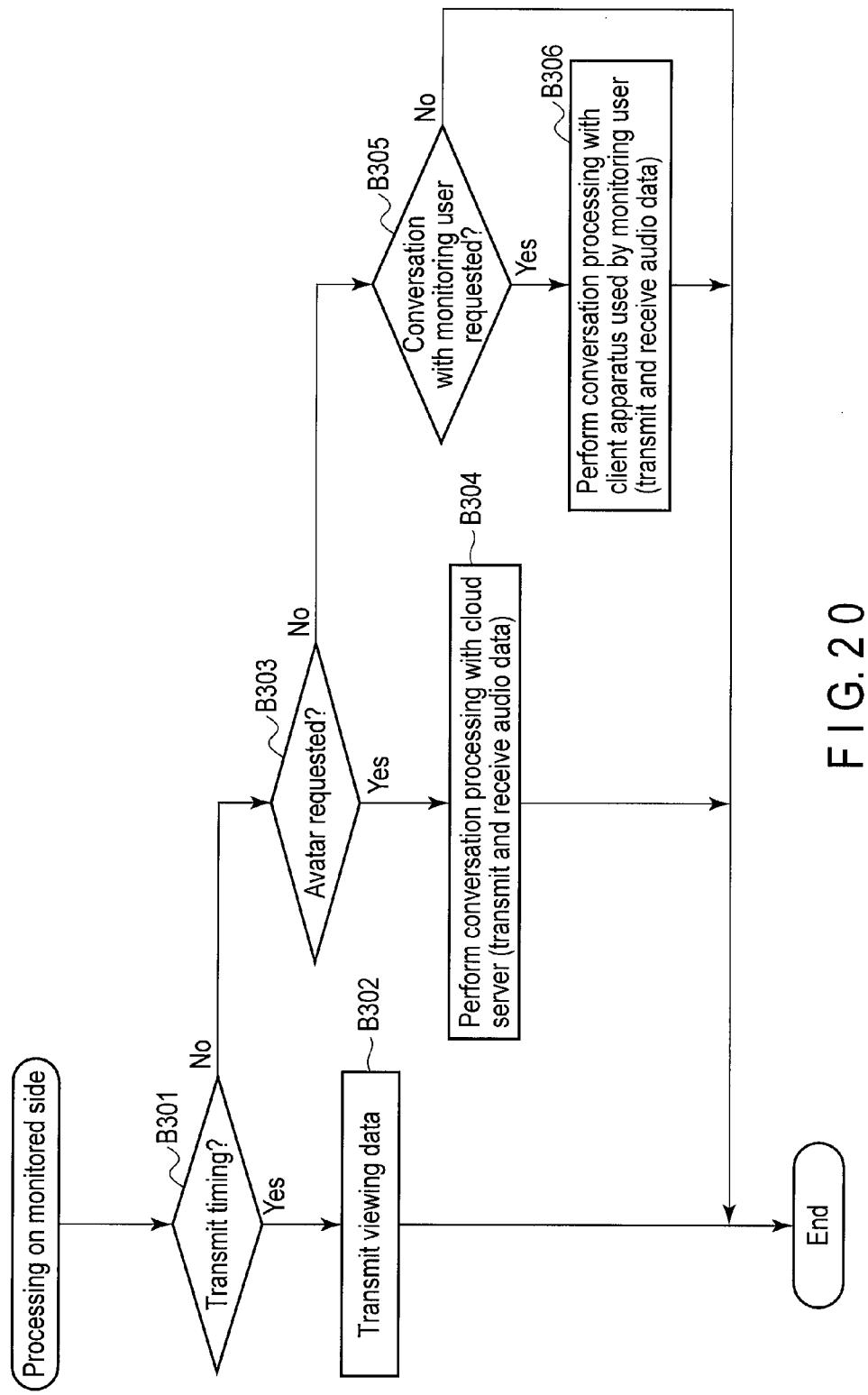
FIG. 20 is a flowchart illustrating an example of the procedure of a process executed by the electronic apparatus (TV) used by the monitored user of FIG. 18.

Processing when data for supporting a conversation with the monitored user is transmitted from the cloud server 1A to the client 3B, 3C used by the monitoring user will be described with reference to FIGS. 20 to 22.

First, the procedure of processing on the side of the monitored user will be described with reference to the flowchart of FIG. 20.

First, the TV 2A used by the monitored user determines whether data should be transmitted at this time or not (block B301). If the data should be transmitted at this time (Yes in block B301), the transmitter 252 of the TV 2A transmits viewing data to the cloud server 1A (block B302).

If the data should not be transmitted at this time (No in block B301), the conversation processor 255 determines whether an avatar has been requested or not (block B303). The avatar is a program which has a function of holding a conversation with the monitored user and is executed, for example, on the cloud server 1A. If an avatar is requested (Yes in block B303), the conversation processor 255 performs conversation processing with the cloud server 1A. That is, the conversation processor 255 transmits the audio data based on utterances by the monitored user to the cloud server 1A and receives the audio data for utterances by the avatar from the cloud server 1A (block B304). The audio data based on the utterances of the monitored user is generated using, for example, the microphone 220. In addition, the received audio data for the utterances by the avatar is played (output) using, for example, the speaker 211.

If an avatar has not been requested (No in block B303), the conversation processor 255 determines whether conversation with the monitoring user has been requested or not (block B305). If conversation with the monitoring user has been requested (Yes in block B305), the conversation processor 255 performs conversation processing between the TV 2A and the client 3B, 3C used by the monitoring user. That is, the conversation processor 255 transmits the audio data based on the utterances by the monitored user to the client 3B, 3C, and receives the audio data based on the utterances by the monitoring user from the client 3B, 3C (block B306). If conversation with the monitoring user is not requested (No in block B305), the processing is terminated.

Figure 21:
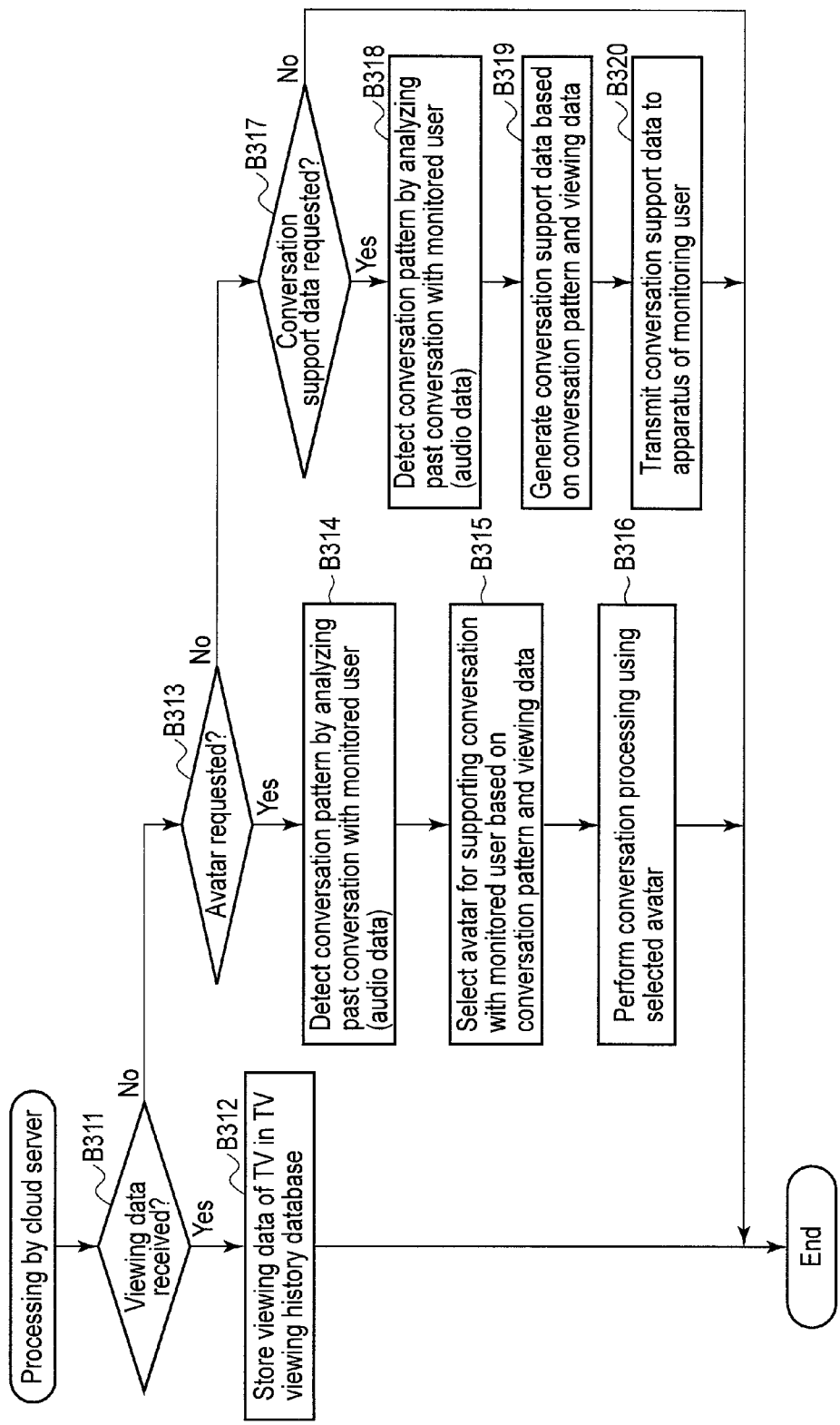
FIG. 21 is a flowchart illustrating the third example of the procedure of a process executed by the electronic apparatus according to the embodiment.
Figure 22:
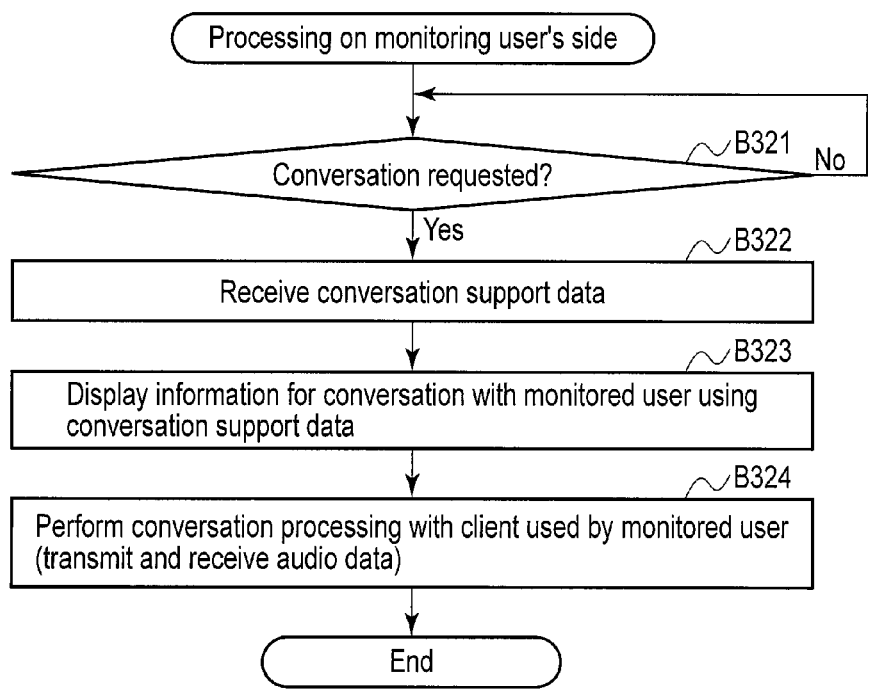
FIG. 22 is a flowchart illustrating an example of the procedure of a process executed by the electronic apparatus used by the monitoring user of FIG. 18.

The flowchart of FIG. 21 illustrates the procedure of monitoring processing by the cloud server 1A.

The receiver 151 of the cloud server 1A determines whether the viewing data of the TV 2A used by the monitored user is received or not (block B311). If the viewing data is received (Yes in block B311), the receiver 151 stores the received viewing data of the TV 2A in the TV viewing history database 1B (block B312).

If the viewing data has not been received (No in block B311), the voice recognition and pattern analyzer 158 determines whether an avatar has been requested or not (block B313). If an avatar has not been requested (Yes in block B313), the voice recognition and pattern analyzer 158 analyzes a past conversation with the monitored user (audio data) to detect a conversation pattern (block B314).

Then, the avatar controller (conversation processor) 157 selects an avatar for supporting the conversation with the monitored user based on the conversation pattern and viewing data of the monitored user (block B315). The avatar controller 157 performs the conversation processing with the monitored user using the selected avatar (block B316). It should be noted that the voice recognition and pattern analyzer 158 may update the conversation pattern using the audio data of the conversation with the monitored user newly obtained by the conversation processing in block B316.

If an avatar has not been requested (No in block B313), the voice recognition and pattern analyzer 158 determines whether the conversation support data has been requested or not (block B317). The voice recognition and pattern analyzer 158 determines whether the conversation support data has been requested, for example, from the client 3B, 3C used by the monitoring user.

If the conversation support data has been requested (Yes in block B317), the voice recognition and pattern analyzer 158 analyzes a past conversation with the monitored user (audio data) to detect the conversation pattern (block B318). The conversation support data generator 160 generates the conversation support data based on the conversation pattern and the viewing data (block B319). The transmitter 154 transmits the generated conversation support data to the client 3B, 3C used by the monitoring user (block B320).

The procedure of display control processing by the client 3A on the side of the monitoring user will be described with reference to the flowchart of FIG. 22.

First, the monitoring data receiver 313 determines whether a conversation is requested or not (block B321). The monitoring data receiver 313 determines that the conversation is requested when an operation for starting the conversation by the monitoring user is detected, or when a request for a start of the conversation is received from the TV 2A used by the monitored user. If the conversation is not requested (No in block B321), the procedure returns to block B321, and whether the conversation is requested or not is determined again.

If the conversation is requested (Yes in block B321), the monitoring data receiver 313 receives conversation support data from the cloud server 1A (block B322). The display processor 315 displays information for supporting the conversation with the monitored user on a screen using the conversation support data (block B323). Then, the conversation processor 316 performs the conversation processing with the client (TV) 2A used by the monitored user. That is, the conversation processor 31 transmits the audio data based on the utterances by the monitoring user to the client (TV) 2A, and receives the audio data based on the utterances by the monitored user from the client (TV) 2A (block B324).

Next, FIG. 23 illustrates a case where the state of health of the monitored user (elderly person) is indicated to the monitoring user (family) by the cloud server 1A.

The TV 2A used by the monitored user stores viewing data indicating a program viewed by the monitored user in the TV viewing history database 1B through the network 4. The TV viewing history database 1B accumulates, for example, electronic program guide (EPG) data and the monitored user's viewing data during a given period. The cloud server 1A receives the viewing data indicating the program viewed by the monitored user from the TV viewing history database 1B by accessing the TV viewing history database 1B through the network 4.

Also, the TV 2A generates an image of the monitored user using the camera 219 connected to or embedded in the TV 2A. The image is stored, for example, in a storage medium in the TV 2A. The TV 2A can make an album or a personal history of the monitored user using the stored image. The TV 2A can also display a contact list made by the monitored user in advance, a memo for a family, a will, etc. on a screen.

Further, the TV 2A detects motion of the monitored user using a plurality of images (a moving image) continuously captured by the camera 219. The TV 2A transmits motion data indicating the detected motion to the cloud server 1A.

The cloud server 1A estimates the state of health of the monitored user using the received viewing data and motion data. The state of health indicates, for example, soundness of health of the monitored user. The cloud server 1A transmits the estimated state-of-health data of the monitored user to the client 3B, 3C used by the monitoring user through the network 4.

The client 3B, 3C indicate the state of health of the monitored user to the monitoring user using the received state-of-health data. A user (monitoring user) using the client 3B, 3C can confirm the state of health of the monitored user by the indication.

A fourth example of the functional configuration of the monitoring server program 112 executed on the cloud server 1A will be described with reference to FIG. 24. The monitoring server program 112 includes, for example, the receiver 151, the transmitter 154 and a state-of-health estimator 161.

The receiver 151 receives data from the TV 2A used by the monitored user. More specifically, the receiver 151 receives the motion data and viewing data transmitted from the transmitter 252 in the TV 2A. The motion data of the TV 2A indicates the motion of the monitored user. The motion of the monitored user is calculated by an analysis of a plurality of images by a motion detector 256 in the TV 2A which are continuously captured by the camera module 219. The motion detector 256 detects the motion of the monitored user, for example, based on a difference between the images, and then estimates an amount of activity of the monitored user based on the amount of motion (difference between the images).

Also, the viewing data of the TV 2A includes a date and time of broadcast, a title, a channel, a category (genre), etc., of the program viewed by the monitored user. The viewing data is generated by the viewing data generator 251 in the TV 2A, for example, when the program is viewed by the monitored user.

The receiver 151 stores the received motion data in a storage medium, etc. The receiver 151 also stores the received viewing data of the TV 2A in the TV viewing history database 1B. The configuration of the viewing data stored in the TV viewing history database 1B is similar to that shown in FIG. 8.

Next, the state-of-health estimator 161 generates the state-of-health data concerning the monitored user at predetermined intervals (for example, everyday) or in response to a request of the client 3B, 3C used by the monitoring user. More specifically, the state-of-health estimator 161 estimates the state of health of the monitored user using the motion data of the monitored user and the viewing data stored in the TV viewing history database 1B. The state-of-health estimator 161 estimates the state of health of the monitored user, for example, based on whether the program is viewed on the TV 2A or not, whether the amount of activity of the monitored user is greater than or equal to a threshold value or not, etc.

The transmitter 154 transmits the state-of-health data indicating the estimated state of health to the client 3B, 3C used by the monitoring user.

In the client 3B, 3C used by the monitoring user, the monitoring client program 213A configured to receive the state-of-health data from the cloud server 1A and to indicate information based on the state-of-health data to a user is executed. The monitoring client program 213A includes, for example, the monitoring data receiver 313 and the display processor 315.

The monitoring data receiver 313 receives the state-of-health data from the cloud server 1A (transmitter 154).

Then, the display processor 315 displays the information indicating the state of health of the monitored user on a screen using the state-of-health data. In addition, the display processor 315 can indicate that the current state of health is unusual when the current state of health is different from usual state (i.e., when it is estimated that the state of health is poor). The display processor 315 indicates the poor state of health by, for example, an eye-catching color, mark, etc. It should be noted that the poor state of health may be indicated by audio or an alarm.

Figure 25:
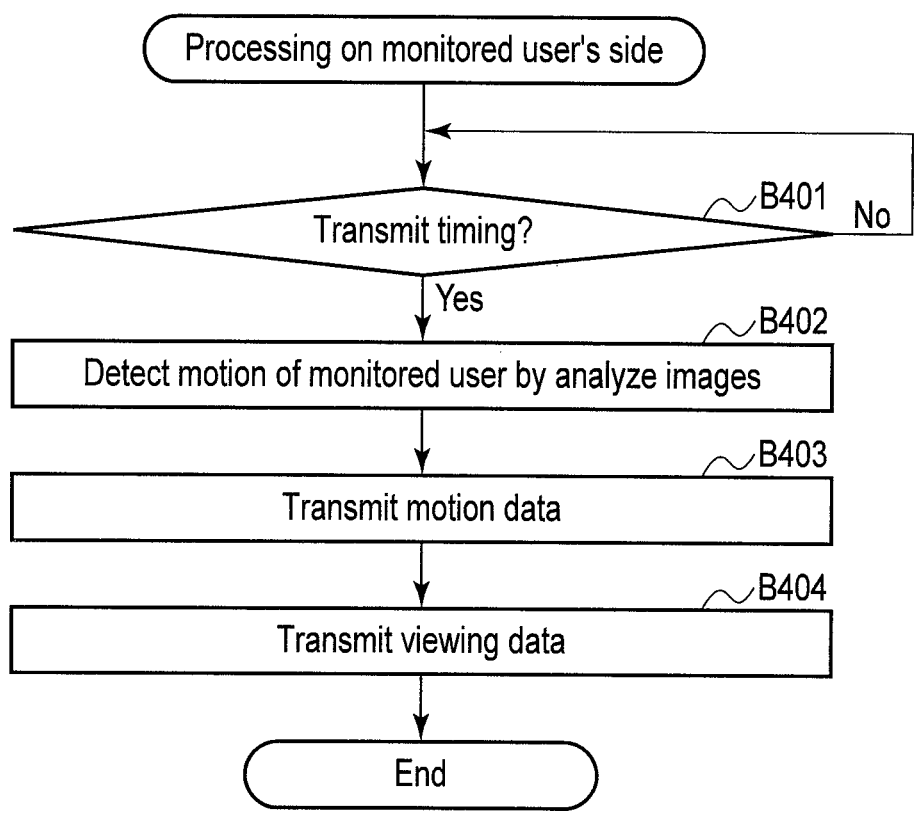
FIG. 25 is a flowchart illustrating an example of the procedure of a process executed by the electronic apparatus (TV) used by the monitored user of FIG. 23.

Processing when data indicating the state of health of the monitored user is transmitted from the cloud server 1A to the client 3B, 3C used by the monitoring user will be described with reference to FIGS. 25 to 27.

First, the procedure of processing on the side of the monitored user will be described with reference to the flowchart of FIG. 25.

First, the TV 2A used by the monitored user determines whether data should be transmitted at this time or not (block B401). If the data should not be transmitted at this time (No in block B401), the procedure returns to block B401, and whether the data should be transmitted at this time or not is determined again.

If the data should be transmitted at this time (Yes in block B401), the motion detector 256 of the TV 2A detects motion of the monitored user by analyzing images captured by the camera module 219 (block B402). Then, the transmitter 252 of the TV 2A transmits the motion data indicating the detected motion to the cloud server 1A (block B403). The transmitter 252 of the TV 2A also transmits the viewing data to the cloud server 1A (block B404).

Figure 26:
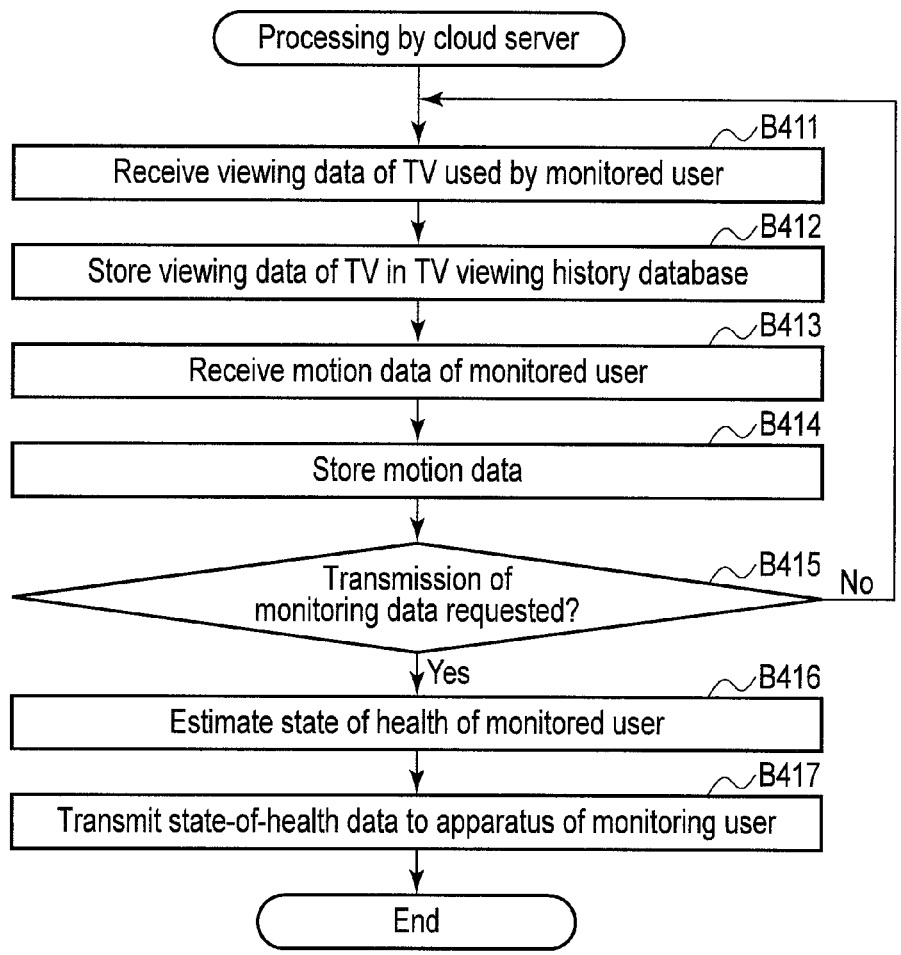
FIG. 26 is a flowchart illustrating the fourth example of the procedure of a process executed by the electronic apparatus according to the embodiment.
Figure 27:
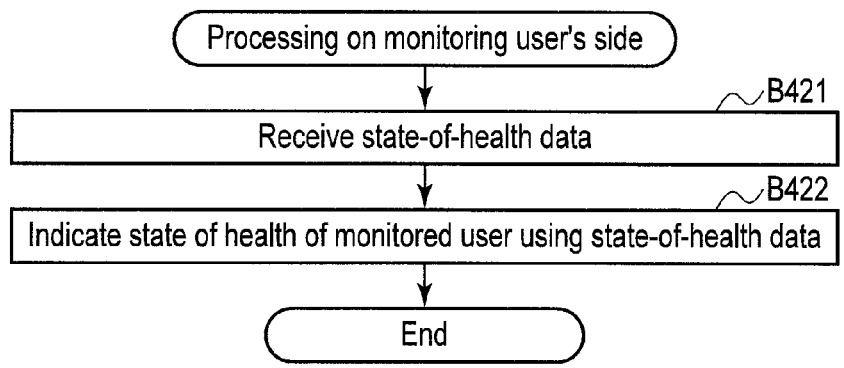
FIG. 27 is a flowchart illustrating an example of the procedure of a process executed by the electronic apparatus used by the monitoring user of FIG. 23.

The flowchart of FIG. 26 illustrates the procedure of monitoring processing by the cloud server 1A.

The receiver 151 of the cloud server 1A receives viewing data of the TV 2A used by the monitored user (block B411). The receiver 151 stores the received viewing data of the TV 2A in the TV viewing history database 1B (block B412). The receiver 151 also receives the motion data of the monitored user (block B413). Then, the receiver 151 stores the received motion data in a storage medium, etc. (block B414).

Next, the state-of-health estimator 161 determines whether the client 3B, 3C used by the monitoring user requests transmission of monitoring data or not by (block B415). If the transmission of the monitoring data is not requested (No in block B415), the procedure returns to block B411, and the processing of receiving data from the TV 2A used by the monitored user continues.

If the transmission of the monitoring data is requested (Yes in block B415), the state-of-health estimator 161 estimates the state of health of the monitored user using the stored motion data of the monitored user and the viewing data stored in the TV viewing history database 1B (block B416). Then, the transmitter 154 transmits the state-of-health data (monitoring data) indicating the estimated state of health to the client 3B, 3C used by the monitoring user (block B417).

The procedure of display control processing by the client 3B, 3C on the side of the monitoring user will be described with reference to the flowchart of FIG. 27.

The monitoring data receiver 313 receives the state-of-health data from the cloud server 1A (block B421). Then, the display processor 315 indicates the state of health of the monitored user using the state-of-health data (block B422). The display processor 315 displays, for example, a text, an image, etc., representing the state of health on a screen. It should be noted that the state of health of the monitored user may be indicated by audio.

The monitoring data, the conversation support data and the state-of-health data supplied from the cloud server 1A to the clients 3A, 3B, 3C may be described, for example, in HTML which can be displayed on a web browser. In this case, the information (web page) corresponding to the received data is displayed on a screen by the web browser executed on the clients 3A, 3B, 3C.

As described above, according to this embodiment, when the information for monitoring a user is provided, the stress placed on the monitored user or the monitoring user can be reduced. It should be noted that an example of offering various items of information for monitoring the user is indicated in the above description. One of the items of information can be provided to the monitoring user. Alternatively, some of the pieces of information can be combined to be provided to the monitoring user.

Also, all the processing procedures according to this embodiment which are described in the flowcharts of FIGS. 9 to 11, 15 to 17, 20 to 22, and 25 to 27 can be executed by software. Thus, an advantage similar to that of this embodiment can be easily obtained merely by installing a program for executing the processing procedures on a normal computer through a computer-readable storage medium having the program stored thereon, and executing the program.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic apparatus comprising:
   a receiver configured to receive operation data indicative of an operating period from each of one or more electronic apparatuses used by a first user, and to receive viewing data from a first electronic apparatus of the one or more electronic apparatuses, the viewing data indicative of a program viewed by the first user;
   a generator configured to (i) estimate a sleep period of the first user using the operation data, (ii) detect a first program frequently viewed by the first user during a current period using the viewing data, and (iii) generate living pattern data indicative of a living pattern of the first user using the operation data and the viewing data, the living pattern data comprising data indicative of the sleep period, the first program and a program currently being viewed by the first user; and
   a transmitter configured to transmit the living pattern data to an electronic apparatus used by a second user.

2. The electronic apparatus of claim 1, wherein the receiver is further configured to receive smile degree data from the first electronic apparatus, the smile degree data comprising a degree indicative of how much the first user smiled when viewing a broadcast program,
   the generator is configured to estimate a biorhythm of the first user using the viewing data and the smile degree data, and
   the living pattern data comprising data indicative of the biorhythm.

3. The electronic apparatus of claim 1, further comprising a controller configured to control an avatar holding a conversation with the first user,
   wherein the generator is further configured to generate conversation support data for supporting the conversation with the first user by analyzing audio data corresponding to a conversation with the first user, and
   the transmitter is configured to transmit the conversation support data to the electronic apparatus used by the second user.

4. The electronic apparatus of claim 1, wherein the receiver is further configured to receive motion data indicative of motion of the first user from the first electronic apparatus,
   the generator is further configured to estimate a state of health of the first user using the viewing data and the motion data, and
   the living pattern data comprising data indicative of the state of health.

5. An electronic apparatus comprising:
   a receiver configured to receive electronic program guide data of a broadcast program and living pattern data indicative of a living pattern of a remote user; and
   a display processor configured to display an electronic program guide that comprises (i) information indicative of the living pattern of the remote user on a screen using the electronic program guide data and the living pattern data, wherein the living pattern data is generated using operation data and viewing data, the operation data indicative of a period during which each of one or more electronic apparatuses used by the remote user operates, the viewing data indicative of a program viewed by the remote user on a first electronic apparatus of the one or more electronic apparatuses, (ii) information indicative of a sleep period of the remote user, (iii) information indicative of a first program frequently viewed by the remote user during a current period, and (iv) information indicative of a program currently being viewed by the remote user.

6. The electronic apparatus of claim 5, wherein the living pattern data comprising data indicative of a biorhythm of the remote user, and
the display processor is further configured to display the biorhythm on the screen.

7. The electronic apparatus of claim 5, wherein the receiver is further configured to receive conversation support data for supporting a conversation with the remote user, and
the display processor displays information based on the conversation support data on the screen.

8. The electronic apparatus of claim 5, wherein the living pattern data comprising data indicative of a state of health of the remote user, and
the display processor is further configured to display the state of health on the screen.

9. A method comprising:
receiving operation data indicative of an operating period from each of one or more electronic apparatuses used by a first user, and receiving viewing data indicative of a program viewed by the first user from a first electronic apparatus of the one or more electronic apparatuses;
estimating a sleep period of the first user using the operation data;
detecting a first program frequently viewed by the first user during a current period using the viewing data;
generating living pattern data indicative of a living pattern of the first user using the operation data and the viewing data, the living pattern data comprising data indicative of the sleep period, the first program and a program currently being viewed by the first user; and
transmitting the living pattern data to an electronic apparatus used by a second user.

10. A method comprising:
receiving electronic program guide data of a broadcast program and living pattern data indicative of a living pattern of a remote user; and
displaying an electronic program guide on a screen using the electronic program guide data and the living pattern data, the electronic program guide comprising information indicative of a sleep period of the remote user, information indicative of a first program frequently viewed by the remote user during a current period, information indicative of a program currently being viewed by the remote user and information indicative of the living pattern of the remote user,
wherein the living pattern data is generated using operation data and viewing data, the operation data indicative of a period during which each of one or more electronic apparatuses used by the remote user operates, the viewing data indicative of a program viewed by the remote user on a first electronic apparatus of the one or more electronic apparatuses.

* * * * *